(12) United States Patent
Prince

(10) Patent No.: US 12,239,986 B2
(45) Date of Patent: Mar. 4, 2025

(54) FLOW CELL WITH ENHANCED WELL IMAGING RESOLUTION

(71) Applicant: ILLUMINA, INC., San Diego, CA (US)

(72) Inventor: Simon Prince, Carlsbad, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 17/898,802

(22) Filed: Aug. 30, 2022

(65) Prior Publication Data

US 2023/0070459 A1   Mar. 9, 2023

Related U.S. Application Data

(60) Provisional application No. 63/239,061, filed on Aug. 31, 2021.

(51) Int. Cl.
| | | |
|---|---|---|
| *B01L 3/00* | (2006.01) | |
| *H04N 23/45* | (2023.01) | |
| *H04N 23/67* | (2023.01) | |

(52) U.S. Cl.
CPC ........ *B01L 3/502784* (2013.01); *H04N 23/45* (2023.01); *B01L 2200/16* (2013.01); *B01L 2300/0654* (2013.01); *B01L 2300/0877* (2013.01); *H04N 23/67* (2023.01)

(58) Field of Classification Search
CPC ..... B01L 2300/0877; B01L 2300/0874; B01L 3/5085

See application file for complete search history.

(56) References Cited

U.S. PATENT DOCUMENTS

| | | |
|---|---|---|
| 5,130,238 A | 7/1992 | Malek et al. |
| 5,185,243 A | 2/1993 | Ullman et al. |
| 5,223,414 A | 6/1993 | Zarling et al. |
| 5,455,166 A | 10/1995 | Walker |
| 5,573,907 A | 11/1996 | Carrino et al. |
| 5,599,675 A | 2/1997 | Brenner |
| 5,641,658 A | 6/1997 | Adams et al. |

(Continued)

FOREIGN PATENT DOCUMENTS

| | | |
|---|---|---|
| CN | 109491176 A | 3/2019 |
| EP | 0320308 B1 | 11/1993 |

(Continued)

OTHER PUBLICATIONS

International Search Report and Written Opinion dated Dec. 23, 2022, for International Application No. PCT/US2022/041208, 10 pages.

(Continued)

*Primary Examiner* — Natalia Levkovich
(74) *Attorney, Agent, or Firm* — FROST BROWN TODD LLP

(57) ABSTRACT

Resolution of images used in processes such as sequencing by synthesis may be increased by structuring sites that would emit signals in the images to have different elevations. Differences in focus caused by these differences in elevation may be used to filter out background illumination, thereby providing an image in which in focus sites may be resolved even though the separation between any site and its nearest neighbor may be below the diffraction limit of the light that would be emitted.

13 Claims, 19 Drawing Sheets

(56) References Cited

U.S. PATENT DOCUMENTS

| | | | |
|---|---|---|---|
| 5,679,524 | A | 10/1997 | Nikiforov et al. |
| 5,750,341 | A | 5/1998 | Macevicz |
| 6,210,891 | B1 | 4/2001 | Nyren et al. |
| 6,214,587 | B1 | 4/2001 | Dattagupta et al. |
| 6,258,568 | B1 | 7/2001 | Nyren |
| 6,266,459 | B1 | 7/2001 | Walt et al. |
| 6,274,320 | B1 | 8/2001 | Rothberg |
| 6,355,431 | B1 | 3/2002 | Chee et al. |
| 6,770,441 | B2 | 8/2004 | Dickinson et al. |
| 6,859,570 | B2 | 2/2005 | Walt et al. |
| 7,057,026 | B2 | 6/2006 | Barnes et al. |
| 7,115,400 | B1 | 10/2006 | Adessi et al. |
| 7,195,872 | B2 | 3/2007 | Agrawal et al. |
| 7,211,414 | B2 | 5/2007 | Hardin et al. |
| 7,244,559 | B2 | 7/2007 | Rothberg |
| 7,315,019 | B2 | 1/2008 | Turner et al. |
| 7,323,305 | B2 | 1/2008 | Leamon et al. |
| 7,329,492 | B2 | 2/2008 | Hardin et al. |
| 7,329,860 | B2 | 2/2008 | Feng et al. |
| 7,622,294 | B2 | 11/2009 | Walt et al. |
| 7,741,463 | B2 | 6/2010 | Gormley et al. |
| 7,940,282 | B2 | 5/2011 | Milanfar et al. |
| 8,345,144 | B1 | 1/2013 | Georgiev et al. |
| 8,749,694 | B2 | 6/2014 | Georgiev et al. |
| 8,759,037 | B2 | 6/2014 | Rigatti et al. |
| 8,778,848 | B2 | 7/2014 | Lin et al. |
| 8,778,849 | B2 | 7/2014 | Bowen et al. |
| 8,895,249 | B2 | 11/2014 | Shen et al. |
| 8,906,320 | B1 | 12/2014 | Eltoukhy et al. |
| 8,951,781 | B2 | 2/2015 | Reed et al. |
| 8,965,076 | B2 | 2/2015 | Garcia et al. |
| 9,012,022 | B2 | 4/2015 | George et al. |
| 9,096,899 | B2 | 8/2015 | Eltoukhy et al. |
| 9,193,996 | B2 | 11/2015 | Buermann et al. |
| 9,485,432 | B1 | 11/2016 | Medasani et al. |
| 9,500,846 | B2 | 11/2016 | Betzig et al. |
| 9,512,422 | B2 | 12/2016 | Barnard et al. |
| 9,574,226 | B2 | 2/2017 | Gormley et al. |
| 9,696,534 | B2 | 7/2017 | Shroff et al. |
| 9,800,856 | B2 | 10/2017 | Venkataraman et al. |
| 2002/0055100 | A1 | 5/2002 | Kawashima et al. |
| 2003/0103021 | A1 | 6/2003 | Young et al. |
| 2003/0160181 | A1 | 8/2003 | Corson et al. |
| 2004/0002090 | A1 | 1/2004 | Mayer |
| 2004/0166593 | A1 | 8/2004 | Nolte et al. |
| 2004/0175843 | A1 | 9/2004 | Roitman et al. |
| 2005/0191698 | A1 | 9/2005 | Chee et al. |
| 2006/0057729 | A1 | 3/2006 | Moon et al. |
| 2007/0134784 | A1 | 6/2007 | Halverson et al. |
| 2007/0259365 | A1 | 11/2007 | Hah et al. |
| 2008/0009420 | A1 | 1/2008 | Schroth |
| 2009/0186777 | A1 | 7/2009 | Lee et al. |
| 2011/0059865 | A1 | 3/2011 | Smith et al. |
| 2013/0065794 | A1 | 3/2013 | Law et al. |
| 2013/0096034 | A1 | 4/2013 | Lebl et al. |
| 2013/0144217 | A1 | 6/2013 | Ross |
| 2014/0243224 | A1 | 8/2014 | Barnard et al. |
| 2015/0293021 | A1 | 10/2015 | Finkelstein et al. |
| 2016/0019693 | A1 | 1/2016 | Silbersweig |
| 2017/0274374 | A1* | 9/2017 | Bowen ................. B01L 3/5085 |
| 2021/0222238 | A1 | 7/2021 | Chen et al. |

FOREIGN PATENT DOCUMENTS

| | | | |
|---|---|---|---|
| EP | | 0336731 B1 | 5/1994 |
| EP | | 0439182 B1 | 4/1996 |
| EP | | 2374902 A1 | 10/2011 |
| EP | | 2675047 A1 | 12/2013 |
| WO | WO 1989/012696 A1 | | 12/1898 |
| WO | WO 1989/009835 A1 | | 10/1989 |
| WO | WO 1989/010977 A1 | | 11/1989 |
| WO | WO 1990/001069 A1 | | 2/1990 |
| WO | WO 1991/006678 A1 | | 5/1991 |
| WO | WO 1997/013633 A1 | | 4/1997 |
| WO | WO 1998/059066 A1 | | 12/1998 |
| WO | WO 2003/101618 A1 | | 12/2003 |
| WO | WO 2004/018497 A2 | | 3/2004 |
| WO | WO 2005/010145 A2 | | 2/2005 |
| WO | WO 2007/123744 A2 | | 11/2007 |
| WO | WO 2010/039147 A1 | | 4/2010 |
| WO | WO 2011/105679 A2 | | 9/2011 |
| WO | WO 2013/154770 A1 | | 10/2013 |
| WO | WO 2014/142841 A1 | | 9/2014 |
| WO | WO 2014/197096 A2 | | 12/2014 |
| WO | WO 2022/256226 A1 | | 12/2022 |
| WO | WO 2023/287617 A1 | | 1/2023 |

OTHER PUBLICATIONS

Bains, William, and Geoff C. Smith. "A novel method for nucleic acid sequence determination." *Journal of theoretical biology* 135.3 (1988): 303-307.

Bentley, David R., et al. "Accurate whole human genome sequencing using reversible terminator chemistry." *nature* 456.7218 (2008): 53-59.

Dean, Frank B., et al. "Comprehensive human genome amplification using multiple displacement amplification." *Proceedings of the National Academy of Sciences* 99.8 (2002): 5261-5266.

Dressman, Devin, et al. "Transforming single DNA molecules into fluorescent magnetic particles for detection and enumeration of genetic variations." *Proceedings of the National Academy of Sciences* 100.15 (2003): 8817-8822.

Drmanac, Snezana, et al. "Accurate sequencing by hybridization for DNA diagnostics and individual genomics." *Nature biotechnology* 16.1 (1998): 54-58.

Fodor, Stephen PA, et al. "Light-directed, spatially addressable parallel chemical synthesis." *science* 251.4995 (1991): 767-773.

Haugland, Richard P., "Molecular Probes Handbook of Fluorescent Probes and Research Chemicals", Sixth Edition, 1996.

Joos, Beda, Herbert Kuster, and Richard Cone. "Covalent attachment of hybridizable oligonucleotides to glass supports." *Analytical biochemistry* 247.1 (1997): 96-101.

Khandjian, Edouard W. "UV crosslinking of RNA to nylon membrane enhances hybridization signals." *Molecular biology reports* 11.2 (1986): 107-115.

Korlach, Jonas, et al. "Selective aluminum passivation for targeted immobilization of single DNA polymerase molecules in zero-mode waveguide nanostructures." *Proceedings of the National Academy of Sciences* 105.4 (2008): 1176-1181.

Korlach, J., Turner, S.W. (2013). Zero-Mode Waveguides. In: Roberts, G.C.K. (eds) Encyclopedia of Biophysics. Springer, Berlin, Heidelberg.

Lage, José M., et al. "Whole genome analysis of genetic alterations in small DNA samples using hyperbranched strand displacement amplification and array—CGH." *Genome research* 13.2 (2003): 294-307.

Lakowicz, Joseph R., ed. *Principles of fluorescence spectroscopy*. Boston, MA: springer US, 2006.

Levene, Michael J., et al. "Zero-mode waveguides for single-molecule analysis at high concentrations." *science* 299.5607 (2003): 682-686.

Lizardi, Paul M., et al. "Mutation detection and single-molecule counting using isothermal rolling-circle amplification." *Nature genetics* 19.3 (1998): 225-232.

Lundquist, Paul M., et al. "Parallel confocal detection of single molecules in real time." *Optics Letters* 33.9 (2008): 1026-1028.

McNally, James G., et al. "Three-dimensional imaging by deconvolution microscopy." *Methods* 19.3 (1999): 373-385.

Oroskar, A. A., et al. "Detection of immobilized amplicons by ELISA-like techniques." *Clinical chemistry* 42.9 (1996): 1547-1555.

Ronaghi, Mostafa, Mathias Uhlén, and Pål Nyrén. "A sequencing method based on real-time pyrophosphate." *Science* 281.5375 (1998): 363-365.

Ronaghi, Mostafa, et al. "Real-time DNA sequencing using detection of pyrophosphate release." *Analytical biochemistry* 242.1 (1996): 84-89.

(56) References Cited

OTHER PUBLICATIONS

Ronaghi, Mostafa. "Pyrosequencing sheds light on DNA sequencing." *Genome research* 11.1 (2001): 3-11.
Shendure, Jay, et al. "Accurate multiplex polony sequencing of an evolved bacterial genome." *Science* 309.5741 (2005): 1728-1732.
Sibarita, Jean-Baptiste. "Deconvolution microscopy." *Microscopy Techniques* (2005): 201-243.
Smith, Steven B., Laura Finzi, and Carlos Bustamante. "Direct mechanical measurements of the elasticity of single DNA molecules by using magnetic beads." *Science* 258.5085 (1992): 1122-1126.
Taylor, D. M., H. Morgan, and C. D'silva. "Characterization of chemisorbed monolayers by surface potential measurements." *Journal of Physics D: Applied Physics* 24.8 (1991): 1443.
Vincent, Myriam, Yan Xu, and Huimin Kong. "Helicase-dependent isothermal DNA amplification." *EMBO reports* 5.8 (2004): 795-800.
Walker, G. T., et al. "A chemiluminescent DNA probe test based on strand displacement amplification." *Molecular Methods for Virus Detection*. Academic Press, 1995. 329-349.
Walker, G. Terrance, et al. "Strand displacement amplification—an isothermal, in vitro DNA amplification technique." *Nucleic acids research* 20.7 (1992): 1691-1696.
International Search Report and Written Opinion dates Aug. 18, 2017, for International Application No. PCT/US2017/024578, 11 pages.

\* cited by examiner

FLOW CELL WITH ENHANCED WELL IMAGING RESOLUTION

This application claims the benefit of and priority to U.S. Provisional Patent Application Ser. No. 63/239,061, filed Aug. 31, 2021, entitled "Flow Cell with Enhanced Well Imaging Resolution," the disclosure of which is incorporated by reference herein.

BACKGROUND

Aspects of the present disclosure relate generally to biological or chemical analysis and more particularly to systems and methods using image sensors for biological or chemical analysis.

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a flow cell channel. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may be emitted from the analytes. Such optical systems may include an arrangement of lenses, filters, and light sources. In other detection systems, the controlled reactions occur immediately over a solid-state imager (e.g., charged-coupled device (CCD) or a complementary metal-oxide-semiconductor (CMOS) detector) that does not require a large optical assembly to detect the fluorescent emissions.

It may be desirable to maximize the number of wells within channels of a flow cell, as doing so may maximize the number of reactions that may be achieved within the channel. To maximize the number of wells within channels of a flow cell, it may be desirable to minimize the distance between adjacent wells. However, increasing the density of wells in a channel of a flow cell may present challenges in achieving a desired resolution using conventional optical systems and image processing techniques.

SUMMARY

Described herein are devices, systems, and methods for obtaining images which may be encountered in systems that perform optical analysis, such as bioassay systems.

An implementation relates to a system comprising a flow cell comprising a plurality of reaction sites, wherein: the plurality of reaction sites comprises a plurality of sets of reaction sites; for each set of reaction sites from the plurality of sets of reaction sites: that set of reaction sites has a corresponding imaging plane; each reaction site comprised by that set of reaction sites has a location on that set of reaction sites' corresponding imaging plane; and no reaction site from any set of reaction sites other than that set of reaction sites has a location on that set of reaction sites' corresponding imaging plane; a set of cameras; and a processor to: obtain a plurality of unfiltered images using the set of cameras, wherein the plurality of unfiltered images comprises, for each set of reaction sites from the plurality of sets of reaction sites, an image corresponding to that set of reaction sites; and for each set of reaction sites from the plurality of sets of reaction sites, determine a derived image corresponding to that set of reaction sites, wherein the derived image corresponding to that set of reaction sites is based on using differences in focus between images from the plurality of unfiltered images to remove signals from reaction sites not comprised by that set of reaction sites while retaining signals from reaction sites comprised by that set of reaction sites; wherein: each set of reaction sites from the plurality of sets of reaction sites is disjoint with all other sets of reaction sites from the plurality of sets of reaction sites; and for each image from the plurality of unfiltered images, that image comprises: signals from reaction sites comprised by the set of reaction sites corresponding to that image; and signals from reaction sites not comprised by the set of reaction sites corresponding to that image In some implementations as described in the second paragraph of this summary, for each reaction site in the plurality of reaction sites, a center-center distance between that reaction site and a nearest reaction site in the plurality of reaction sites is less than a diffraction limit for a wavelength of light used in obtaining the plurality of unfiltered images; and for each set of reaction sites from the plurality of sets of reaction sites, for each reaction site in that set of reaction sites, a center-center distance between that reaction site and a nearest reaction site in that set of reaction sites is greater than the diffraction limit for the wavelength of light used in obtaining the plurality of unfiltered images.

In some implementations as described in any of the second or third paragraphs of this summary, for each set of reaction sites from the plurality of sets of reaction sites, the set of cameras comprises a corresponding camera focused that set of reaction sites' corresponding imaging plane.

In some implementations such as described in the fourth paragraph of this summary, the system comprises one or more beam splitters to direct signals from the plurality of reaction sites to the cameras from the set of cameras.

In some implementations such as described in any of the second or third paragraphs of this summary, obtaining the plurality of unfiltered images comprises: using a first camera from the set of cameras, capturing an unfiltered first image, wherein the first unfiltered image corresponds to a first set of reaction sites from the plurality of sets of reaction sites, and wherein the first camera is focused on the imaging plane corresponding to the first set of reaction sites when it is used to capture the first unfiltered image; refocusing the first camera on the imaging plane corresponding to a second set of reaction sites from the plurality of sets of reaction sites; and using the first camera, capturing a second unfiltered image, wherein the second unfiltered image corresponds to the second set of reaction sites, and wherein the first camera is focused on the imaging plane corresponding to the second set of reaction sites when it is used to capture the second unfiltered image.

In some implementations such as described in any of the second or third paragraphs of this summary, the set of cameras comprises a line scan camera; the line scan camera comprises a plurality of sets of sensors, wherein, for each set of sensors from the plurality of sets of sensors: that set of sensors has a corresponding set of reaction sites from the plurality of sets of reaction sites; and that set of sensors is focused on the corresponding imaging plane of its corresponding set of reaction sites; and obtaining the plurality of unfiltered images using the set of cameras comprises: capturing a first unfiltered image using a first set of sensors, wherein the first set of sensors corresponds to a first set of reaction sites from the plurality of sets of reaction sites; and capturing a second unfiltered image using a second set of sensors, wherein the second set of sensors corresponds to a second set of reaction sites from the plurality of sets of reaction sites.

In some implementations such as described in any of the second through seventh paragraphs of this summary, each set of reaction sites from the plurality of sets of reaction sites has a corresponding point spread function; and for each set of reaction sites from the plurality of sets of reaction sites, determining the derived image corresponding to that set of reaction sites comprises, for each other set of reaction sites from the plurality of sets of reaction sites, removing signals from reaction sites comprised by that other set of reaction sites using the unfiltered image corresponding to that other set of reaction sites and the point spread function corresponding to that other set of reaction sites.

In some implementations such as described in the eighth paragraph of this summary, for at least one set of reaction sites from the plurality of sets of reaction sites, the corresponding point spread function for that set of reaction sites is different from the corresponding point spread functions for all other sets of reaction sites from the plurality of sets of reaction sites.

In some implementations such as described in the eighth paragraph of this summary, for at least one set of reaction sites from the plurality of sets of reaction sites, the corresponding point spread function for that set of reaction sites is the same as the corresponding point spread function for at least one other set of reaction sites from the plurality of sets of reaction sites.

In some implementations such as described in any of the second through tenth paragraphs of this summary, the plurality of sets of reaction sites consists of two sets of reaction sites.

In some implementations such as described in any of the second through tenth paragraphs of this summary, the plurality of reaction sites comprises three or more sets of reaction sites.

In some implementations such as described in any of the second through twelfth paragraphs of this summary, for each set of reaction sites from the plurality of sets of reaction sites, for each reaction site comprised by that set of reaction sites, that reaction site is located in a corresponding well comprised by the flow cell.

In some implementations such as described in any of the second through twelfth paragraphs of this summary, for each set of reaction sites from the plurality of sets of reaction sites, for each reaction site comprised by that set of reaction sites, that reaction site is located on a vertical location on a corresponding post comprised by the flow cell.

An implementation relates to a method comprising: obtaining a plurality of unfiltered images using a set of cameras, wherein each image from the plurality of unfiltered images is captured by detecting light emitted by a plurality of reaction sites comprised by a flow cell; the plurality of reaction sites comprises a plurality of sets of reaction sites; for each set of reaction sites from the plurality of sets of reaction sites: that set of reaction sites has a corresponding imaging plane; each reaction site comprised by that set of reaction sites has a location on that set of reaction sites' corresponding imaging plane; and no reaction site from any set of reaction sites other than that set of reaction sites has a location on that set of reaction sites' corresponding imaging plane; each unfiltered image from the plurality of unfiltered images has a corresponding set of reaction sites from the plurality of sets of reaction sites; and for each set of reaction sites from the plurality of sets of reaction sites, determining a derived image corresponding to that set of reaction sites based on using differences in focus between images from the plurality of unfiltered images to remove signals from reaction sites not comprised by that set of reaction sites while retaining signals from reaction sites comprised by that set of reaction sites; wherein: each set of reaction sites from the plurality of sets of reaction sites is disjoint with all other sets of reaction sites from the plurality of sets of reaction sites; and for each image from the plurality of unfiltered images, that image comprises: signals from reaction sites comprised by the set of reaction sites corresponding to that image; and signals from reaction sites not comprised by the set of reaction sites corresponding to that image.

In some implementations such as described in the fifteenth paragraph of this summary, for each reaction site in the plurality of reaction sites, a center-center distance between that reaction site and a nearest reaction site in the plurality of reaction sites is less than a diffraction limit for a wavelength of light used in obtaining the plurality of unfiltered images; and for each set of reaction sites from the plurality of sets of reaction sites, for each reaction site in that set of reaction sites, a center-center distance between that reaction site and a nearest reaction site in that set of reaction sites is greater than the diffraction limit for the wavelength of light used in obtaining the plurality of unfiltered images.

In some implementations such as described in any of the fifteenth or sixteenth paragraphs of this summary, for each set of reaction sites from the plurality of sets of reaction sites, the set of cameras comprises a corresponding camera focused that set of reaction sites' corresponding imaging plane.

In some implementations such as described in any of the fifteenth or sixteenth paragraphs of this summary, obtaining the plurality of unfiltered images comprises: using a first camera from the set of cameras, capturing an unfiltered first image, wherein the first unfiltered image corresponds to a first set of reaction sites from the plurality of sets of reaction sites, and wherein the first camera is focused on the imaging plane corresponding to the first set of reaction sites when it is used to capture the first unfiltered image; refocusing the first camera on the imaging plane corresponding to a second set of reaction sites from the plurality of sets of reaction sites; and using the first camera, capturing a second unfiltered image, wherein the second unfiltered image corresponds to the second set of reaction sites, and wherein the first camera is focused on the imaging plane corresponding to the second set of reaction sites when it is used to capture the second unfiltered image.

In some implementations such as described in any of the fifteenth or sixteenth paragraphs of this summary, the set of cameras comprises a line scan camera; the line scan camera comprises a plurality of sets of sensors, wherein, for each set of sensors from the plurality of sets of sensors: that set of sensors has a corresponding set of reaction sites from the plurality of sets of reaction sites; and that set of sensors is focused on the corresponding imaging plane of its corresponding set of reaction sites; and obtaining the plurality of unfiltered images using the set of cameras comprises: capturing a first unfiltered image using a first set of sensors, wherein the first set of sensors corresponds to a first set of reaction sites from the plurality of sets of reaction sites; and capturing a second unfiltered image using a second set of sensors, wherein the second set of sensors corresponds to a second set of reaction sites from the plurality of sets of reaction sites.

In some implementations such as described in any of the fifteenth through nineteenth paragraphs of this summary, each set of reaction sites from the plurality of sets of reaction sites has a corresponding point spread function; and for each set of reaction sites from the plurality of sets of reaction sites, determining the derived image corresponding to that set of reaction sites comprises, for each other set of reaction sites from the plurality of sets of reaction sites, removing signals from reaction sites comprised by that other set of reaction sites using the unfiltered image corresponding to that other set of reaction sites and the point spread function corresponding to that other set of reaction sites.

In some implementations such as described in the twentieth paragraph of this summary, for at least one set of reaction sites from the plurality of sets of reaction sites, the corresponding point spread function for that set of reaction sites is different from the corresponding point spread functions for all other sets of reaction sites from the plurality of sets of reaction sites.

In some implementations such as described in the twentieth paragraph of this summary, for at least one set of reaction sites from the plurality of sets of reaction sites, the corresponding point spread function for that set of reaction sites is the same as the corresponding point spread function for at least one other set of reaction sites from the plurality of sets of reaction sites.

In some implementations such as described in any of the fifteenth through twenty second paragraphs of this summary, for each set of reaction sites from the plurality of sets of reaction sites, for each reaction site comprised by that set of reaction sites, that reaction site is located in a corresponding well comprised by the flow cell.

In some implementations such as described in any of the fifteenth through twenty second paragraphs of this summary, for each set of reaction sites from the plurality of sets of reaction sites, for each reaction site comprised by that set of reaction sites, that reaction site is located on a vertical location on a corresponding post comprised by the flow cell.

An implementation relates to a machine comprising: means for obtaining a plurality of differently focused unfiltered images based on signals from reaction sites comprised by a flow cell; and means for determining a plurality of derived images separating signals from corresponding sets of reaction sites based on differences in focus.

While multiple examples are described, still other examples of the described subject matter will become apparent to those skilled in the art from the following detailed description and drawings, which show and describe illustrative examples of disclosed subject matter. As will be realized, the disclosed subject matter is capable of modifications in various aspects, all without departing from the spirit and scope of the described subject matter. Accordingly, the drawings and detailed description are to be regarded as illustrative in nature and not restrictive.

DETAILED DESCRIPTION

Figure 1:
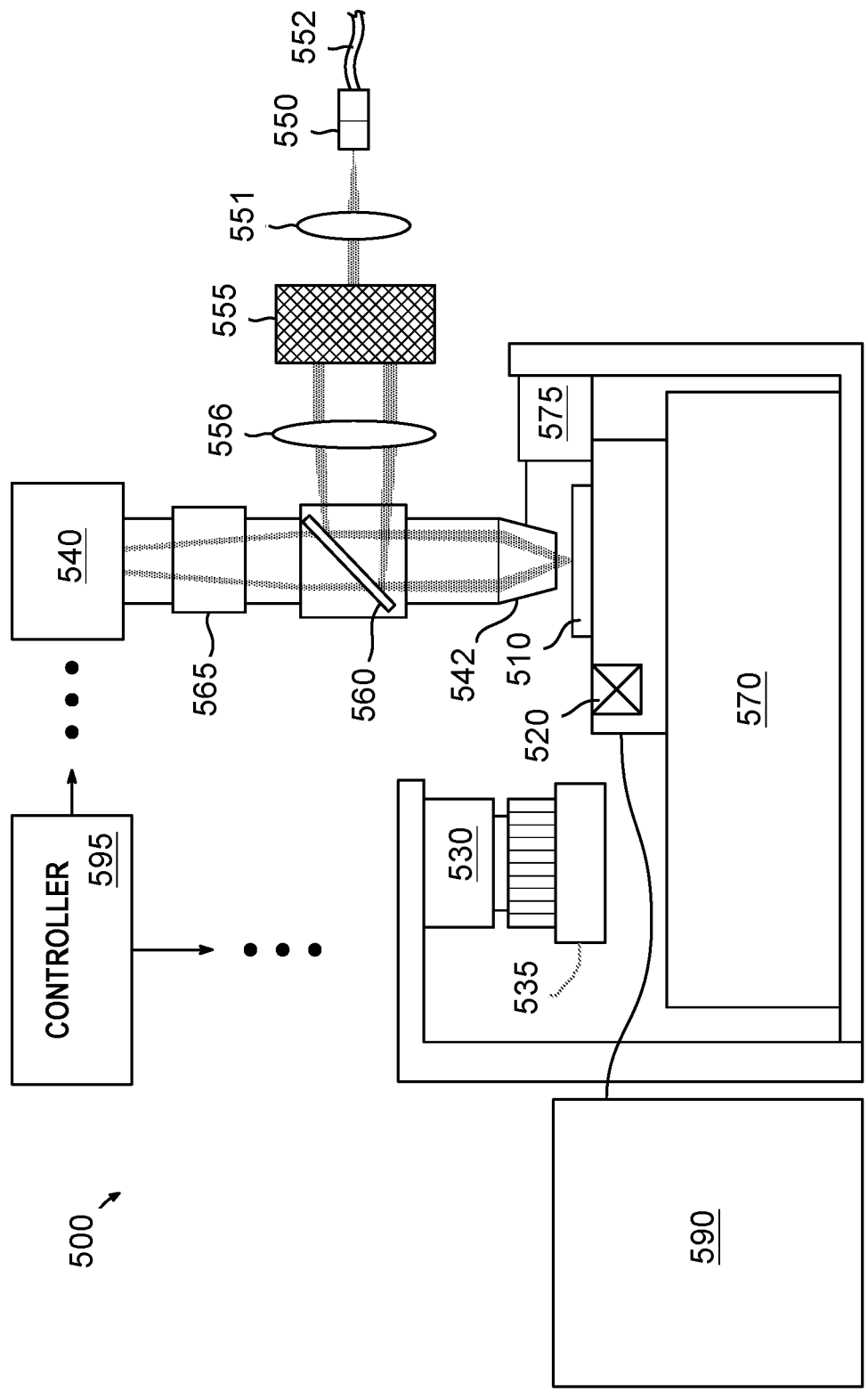
FIG. 1 depicts a schematic diagram of an example of an imaging system that may be implemented in a system for biological or chemical analysis.

I. Overview of System for Biological or Chemical Analysis

Examples described herein may be used in various biological or chemical processes and systems for academic or commercial analysis. More specifically, examples described herein may be used in various processes and systems where it is desired to detect an event, property, quality, or characteristic that is indicative of a designated reaction.

The bioassay systems may be configured to perform a plurality of designated reactions that may be detected individually or collectively. The biosensors and bioassay systems may be configured to perform numerous cycles in which the plurality of designated reactions occurs in parallel. For example, the bioassay systems may be used to sequence a dense array of DNA features through iterative cycles of enzymatic manipulation and image acquisition. The cartridges and biosensors may include one or more microfluidic channels that deliver reagents or other reaction components to a reaction site. In some examples, the reaction sites are randomly distributed across a substantially planar surface. For example, the reaction sites may have an uneven distribution in which some reaction sites are located closer to each other than other reaction sites. In other examples, the reaction sites are patterned across a substantially planar surface in a predetermined manner. Each of the reaction sites may be associated with one or more image sensors that detect light from the associated reaction site. Yet in other examples, the reaction sites are located in reaction chambers that compartmentalize the designated reactions therein.

In some examples, image sensors may detect light emitted from reaction sites and the signals indicating photons emitted from the reaction sites and detected by the individual image sensors may be referred to as those sensors' illumination values. These illumination values may be combined into an image indicating photons as detected from the reaction sites. Such an image may be referred to as an unfiltered image. Similarly, when an image is composed of values which have been processed, such as to computationally correct for crosstalk, rather than being composed of the values directly detected by individual image sensors, that image may be referred to as a sharpened image.

The following detailed description of certain examples will be better understood when read in conjunction with the appended drawings. To the extent that the figures illustrate diagrams of the functional blocks of various examples, the functional blocks are not necessarily indicative of the division between hardware components. Thus, for example, one or more of the functional blocks (e.g., processors or memories) may be implemented in a single piece of hardware (e.g., a general purpose signal processor or random access memory, hard disk, or the like). Similarly, the programs may be stand-alone programs, may be incorporated as subroutines in an operating system, may be functions in an installed software package, and the like. It should be understood that the various examples are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one example" are not intended to be interpreted as excluding the existence of additional examples that also incorporate the recited features. Moreover, unless explicitly stated to the contrary, examples "comprising" or "having" an element or a plurality of elements having a particular property may include additional elements whether or not they have that property.

As used herein, a "designated reaction" includes a change in at least one of a chemical, electrical, physical, or optical property (or quality) of an analyte-of-interest. In some examples, the designated reaction is a positive binding event (e.g., incorporation of a fluorescently labeled biomolecule with the analyte-of-interest). More generally, the designated reaction may be a chemical transformation, chemical change, or chemical interaction. In some examples, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a designated reaction. For example, reaction components include reagents, enzymes, samples, other biomolecules, and buffer solutions. The reaction components may be delivered to a reaction site in a solution and/or immobilized at a reaction site. The reaction components may interact directly or indirectly with another substance, such as the analyte-of-interest.

As used herein, the term "reaction site" is a localized region where a designated reaction may occur. A reaction site may include support surfaces of a substrate where a substance may be immobilized thereon. For example, a reaction site may include a substantially planar surface in a channel of a flow cell that has a colony of nucleic acids thereon. The nucleic acids in the colony may have the same sequence, being for example, clonal copies of a single stranded or double stranded template. However, in some examples a reaction site may contain only a single nucleic acid molecule, for example, in a single stranded or double stranded form. Furthermore, a plurality of reaction sites may be randomly distributed along the support surface or arranged in a predetermined manner (e.g., side-by-side in a matrix, such as in microarrays). A reaction site may also include a reaction chamber that at least partially defines a spatial region or volume configured to compartmentalize the designated reaction. As used herein, the term "reaction chamber" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Examples of biosensors including such reaction chambers are described in greater detail in U.S. Pat. No. 9,096,899, entitled "Microdevices and Biosensor Cartridges for Biological or Chemical Analysis and Systems and Methods for the Same," issued Aug. 4, 2015, the disclosure of which is incorporated herein by reference, in its entirety. Reaction sites do not necessarily need to be provided in reaction chambers and may instead be provided on or in any other suitable kind of structure.

In some examples, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some examples, image sensors (e.g., photodiodes) are associated with corresponding reaction sites. An image sensor that is associated with a reaction site is configured to detect light emissions from the associated reaction site when a designated reaction has occurred at the associated reaction site. In some cases, a plurality of image sensors (e.g., several pixels of a camera device) may be associated with a single reaction site. In other cases, a single image sensor (e.g., a single pixel) may be associated with a single reaction site or with a group of reaction sites. Alternatively, any other suitable relationships between the number of pixels and the number of reaction sites may be used. The image sensor, the reaction site, and other features of the biosensor may be configured so that at least some of the light is directly detected by the image sensor without being reflected.

As used herein, the term "adjacent" when used with respect to two reaction sites means no other reaction site is located between the two reaction sites. The term "adjacent" may have a similar meaning when used with respect to adjacent detection paths and adjacent image sensors (e.g., adjacent image sensors have no other image sensor therebetween). In some cases, a reaction site may not be adjacent to another reaction site; but may still be within an immediate vicinity of the other reaction site. A first reaction site may be in the immediate vicinity of a second reaction site when fluorescent emission signals from the first reaction site are detected by the image sensor associated with the second reaction site. More specifically, a first reaction site may be in the immediate vicinity of a second reaction site when the image sensor associated with the second reaction site detects, for example, crosstalk from the first reaction site. Adjacent reaction sites may be contiguous such that they abut each other or the adjacent sites may be non-contiguous having an intervening space between.

As used herein, a "substance" includes items or solids, such as capture beads, as well as biological or chemical substances. As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species.

Biomolecules, samples, and biological or chemical substances may be naturally occurring or synthetic and may be suspended in a solution or mixture within a spatial region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, when the terms "removably" and "coupled" (or "engaged") are used together to describe a relationship between components, the term is intended to mean that a connection between the components is readily separable without destroying or damaging the components. Components are readily separable when the components may be separated from each other without undue effort or a significant amount of time spent in separating the components. For example, components may be removably coupled or engaged in an electrical manner such that the mating contacts of the components are not destroyed or damaged. Components may also be removably coupled or engaged in a mechanical manner such that the features that hold a component are not destroyed or damaged. Components may also be removably coupled or engaged in a fluidic manner such that ports of a component are not destroyed or damaged. The component is not considered to be destroyed or damaged if, for example, only a simple adjustment to the component (e.g., realignment) or a simple replacement (e.g., replacing a nozzle) is required.

As used herein, the term "fluid communication" or "fluidically coupled" refers to two spatial regions being connected together such that a liquid or gas may flow between the two spatial regions. For example, a microfluidic channel may be in fluid communication with a reaction chamber such that a fluid may flow freely into the reaction chamber from the microfluidic channel. The terms "in fluid communication" or "fluidically coupled" allow for two spatial regions being in fluid communication through one or more valves, restrictors, or other fluidic components to control or regulate a flow of fluid through a system.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon.

In some examples, nucleic acids can be attached to a surface and amplified. Examples of such amplification are described in U.S. Pat. No. 7,741,463, entitled "Method of Preparing Libraries of Template Polynucleotides," issued Jun. 22, 2010, the disclosure of which is incorporated by reference herein, in its entirety. In some cases, repeated rounds of extension (e.g., amplification) using an immobilized primer and primer in solution may provide multiple copies of the nucleic acid.

In particular examples, the assay protocols executed by the systems and methods described herein include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood however that non-natural nucleotides, modified nucleotides or analogs of the aforementioned nucleotides can be used.

In examples that include reaction chambers, items or solid substances (including semi-solid substances) may be disposed within the reaction chambers. When disposed, the item or solid may be physically held or immobilized within the reaction chamber through an interference fit, adhesion, or entrapment. Examples of items or solids that may be disposed within the reaction chambers include polymer beads, pellets, agarose gel, powders, quantum dots, or other solids that may be compressed and/or held within the reaction chamber. In some examples, a nucleic acid superstructure, such as a DNA ball, may be disposed in or at a reaction chamber, for example, by attachment to an interior surface of the reaction chamber or by residence in a liquid within the reaction chamber. A substance that is held or disposed in a reaction chamber can be in a solid, liquid, or gaseous state.

FIG. 1 depicts an example of components of a system 500 that may be used to provide biological or chemical analysis. In some examples, system 500 is a workstation that may be similar to a bench-top device. For example, a majority (or all) of the systems and components for conducting the designated reactions may be within a common housing. In particular examples, system 500 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some versions, system 500 may also be configured to generate reaction sites in a flow cell 510. For example, system 500 may be configured to receive a sample and generate surface attached clusters of clonally amplified nucleic acids derived from the sample.

In particular examples, the system 500 is to perform a large number of parallel reactions within flow cell 510. Flow cell 510 includes one or more reaction sites where designated reactions may occur. The reaction sites may be, for example, immobilized to a solid surface of flow cell 510 or immobilized to beads (or other movable substrates) that are located within corresponding reaction chambers of flow cell 510. The reaction sites may include, for example, clusters of clonally amplified nucleic acids. Flow cell 510 may include one or more flow channels that receive a solution from the system 500 and direct the solution toward the reaction sites. Optionally, flow cell 510 may engage a thermal element for transferring thermal energy into or out of the flow channel.

System 500 may include various components, assemblies, and systems (or sub-systems) that interact with each other to perform a predetermined method or assay protocol for biological or chemical analysis. For example, system 500 includes a system controller 595 that may communicate with the various components, assemblies, and sub-systems of the system 500. Examples of such components are described in greater detail below.

In the present example, a light emitter 550 is configured to output a light beam that is collimated by collimation lens 551. The collimated light is structured (patterned) by light structuring optical assembly 555 and directed by dichroic mirror 560 through objective lens 542 onto a sample of a flow cell 510, which is positioned on a motion stage 570. In the case of a fluorescent sample, the sample fluoresces in response to the structured excitation light, and the resultant light is collected by objective lens 542 and directed to an image sensor of camera system 540 to detect fluorescence. During each imaging cycle, imaging system 500 utilizes light structuring optical assembly 555 to acquire a plurality of images at various phases, with the fringe pattern displaced laterally in the modulation direction (e.g., in the x-y plane and perpendicular to the fringes), with this procedure repeated one or more times by rotating the pattern orientation about the optical axis (i.e., with respect to the x-y plane of the sample). The captured images may then be computationally reconstructed to generate a higher resolution image (e.g., an image having about twice the lateral spatial resolution of individual images). System 500 of the present example thus provides structured illumination microscopy (SIM) utilizing spatially structured excitation light to image a biological sample. Alternatively, system 500 may provide any other kind of illumination and/or optical arrangements (e.g., epifluorescence microscopy, etc.). Light structuring optical assembly 555 and the corresponding SIM algorithms may thus be omitted in some variations.

In system 500, light emitter 550 may include an incoherent light emitter (e.g., emit light beams output by one or more excitation diodes), or a coherent light emitter such as emitter of light output by one or more lasers or laser diodes. As illustrated in the example of system 500, light emitter 550 includes an optical fiber 552 for guiding an optical beam to be output. However, other configurations of a light emitter 550 may be used. In some implementations, optical fiber 552 may optically couple to a plurality of different light sources (not shown), each light source emitting light of a different wavelength. Although system 500 is illustrated as having a single light emitter 550, in some implementations multiple light emitters 550 may be included.

In some implementations, system 500 may include a projection lens 556 that may include a lens element to articulate along the z-axis to adjust the structured beam shape and path. For example, a component of the projection lens 556 may be articulated to account for a range of sample thicknesses (e.g., different cover glass thickness) of the sample in container 510.

In the example of system 500, fluid delivery module or device 590 may direct the flow of reagents (e.g., fluorescently labeled nucleotides, buffers, enzymes, cleavage reagents, etc.) to (and through) flow cell 510 and waste valve 520. Flow cell 510 may include one or more substrates upon which the samples are provided. For example, in the case of a system to analyze a large number of different nucleic acid sequences, flow cell 510 may include one or more substrates on which nucleic acids to be sequenced are bound, attached or associated. The substrate may include any inert substrate or matrix to which nucleic acids may be attached, such as for example glass surfaces, plastic surfaces, latex, dextran, polystyrene surfaces, polypropylene surfaces, polyacrylamide gels, gold surfaces, and silicon wafers. In some applications, the substrate is within a channel or other area at a plurality of locations formed in a matrix or array across the flow cell 510. System 500 may also include a temperature station actuator 530 and heater/cooler 535 that may optionally regulate the temperature of conditions of the fluids within the flow cell 510.

In particular implementations, the flow cell 510 may be implemented as a patterned flow cell including a transparent cover plate, a substrate, and a liquid contained therebetween, and a biological sample may be located at an inside surface of the transparent cover plate or an inside surface of the substrate. The flow cell may include a large number (e.g., thousands, millions, or billions) of wells (also referred to as nanowells) or regions that are patterned into a defined array (e.g., a hexagonal array, rectangular array, etc.) into the substrate. Such wells may define reaction chambers providing reaction sites as described above. Each region may form a cluster (e.g., a monoclonal cluster) of a biological sample such as DNA, RNA, or another genomic material which may be sequenced, for example, using sequencing by synthesis. The flow cell may be further divided into a number of spaced apart lanes (e.g., eight lanes), each lane including a hexagonal array of clusters.

Flow cell 510 may be mounted on a sample stage 570 to provide movement and alignment of the flow cell 510 relative to the objective lens 542. The sample stage may have one or more actuators to allow it to move in any of three dimensions. For example, in terms of the Cartesian coordinate system, actuators may be provided to allow stage 570 to move in the x, y, and z directions relative to the objective lens 542, tilt relative to objective lens 542, and/or otherwise move relative to objective lens 542. Movement of stage 570 may allow one or more sample locations on flow cell 510 to be positioned in optical alignment with objective lens 542. Movement of sample stage 570 relative to objective lens 542 may be achieved by moving sample stage 570 itself, the objective lens 542, some other component of system 500, or any combination of the foregoing. Further implementations may also include moving the system 500 over a stationary sample. Alternatively, flow cell 510 may be fixed during imaging.

In some implementations, a focus (z-axis) component 575 may be included to control positioning of the optical components relative to the flow cell 510 in the focus direction (typically referred to as the z axis, or z direction). Focus component 575 may include one or more actuators physically coupled to the optical stage or the sample stage, or both, to move flow cell 510 on sample stage 570 relative to the optical components (e.g., the objective lens 542) to provide proper focusing for the imaging operation. For example, the actuator may be physically coupled to the respective stage such as, for example, by mechanical, magnetic, fluidic or other attachment or contact directly or indirectly to or with the stage. The one or more actuators may be configured to move the stage in the z-direction while maintaining the sample stage in the same plane (e.g., maintaining a level or horizontal attitude, perpendicular to the optical axis). The one or more actuators may also be configured to tilt the stage. This may be done, for example, so that flow cell 510 may be leveled dynamically to account for any slope in its surfaces.

The structured light emanating from a test sample at a sample location being imaged may be directed through dichroic mirror 560 to one or more detectors of camera system 540. In some implementations, a filter switching assembly 565 with one or more emission filters may be included, where the one or more emission filters may be used to pass through particular ranges of emission wavelengths and block (or reflect) other ranges of emission wavelengths. For example, the one or more emission filters may be used to switch between different channels of the imaging system. In a particular implementation, the emission filters may be implemented as dichroic mirrors that direct emission light of different wavelengths to different image sensors of camera system 540.

Camera system 540 may include one or more image sensors to monitor and track the imaging (e.g., sequencing) of flow cell 510. Camera system 540 may be implemented, for example, as a CCD or CMOS image sensor camera, but other image sensor technologies (e.g., active pixel sensor) may be used. While camera system 540 and associated optical components are shown as being positioned above flow cell 510 in FIG. 1, one or more image sensors or other camera components may be incorporated into system 500 in numerous other ways as will be apparent to those skilled in the art in view of the teachings herein. For instance, one or more image sensors may be positioned under flow cell 510 or may even be integrated into flow cell 510.

II. Example of Flow Cell with Multi-Elevation Reaction Site Arrangement

In some versions of flow cell 510, reaction sites are defined in wells that are formed as recesses in a floor surface of a flow channel of flow cell 510, with such wells being configured with the same depth, such that the reaction sites are all at the same elevation within flow cell 510. Some other versions of flow cells may have wells with different depths, thereby providing reaction sites at different elevations. In some instances, providing reaction sites at offset elevations may enable more dense packing of analyte features on a surface than would be resolvable if the combination of arrays were at the same elevation on the surface. For example, in some cases, providing reaction sites at offset elevations may allow for resolution of reaction sites having a pitch which is less than the diffraction limit of the light they would emit in response to excitation. Providing reaction sites at offset elevations may ultimately enable a flow cell to provide more reaction sites, at a higher density, than could otherwise be achieved without the reaction sites being positioned at offset elevations in a flow cell of the same size.

Figure 2:
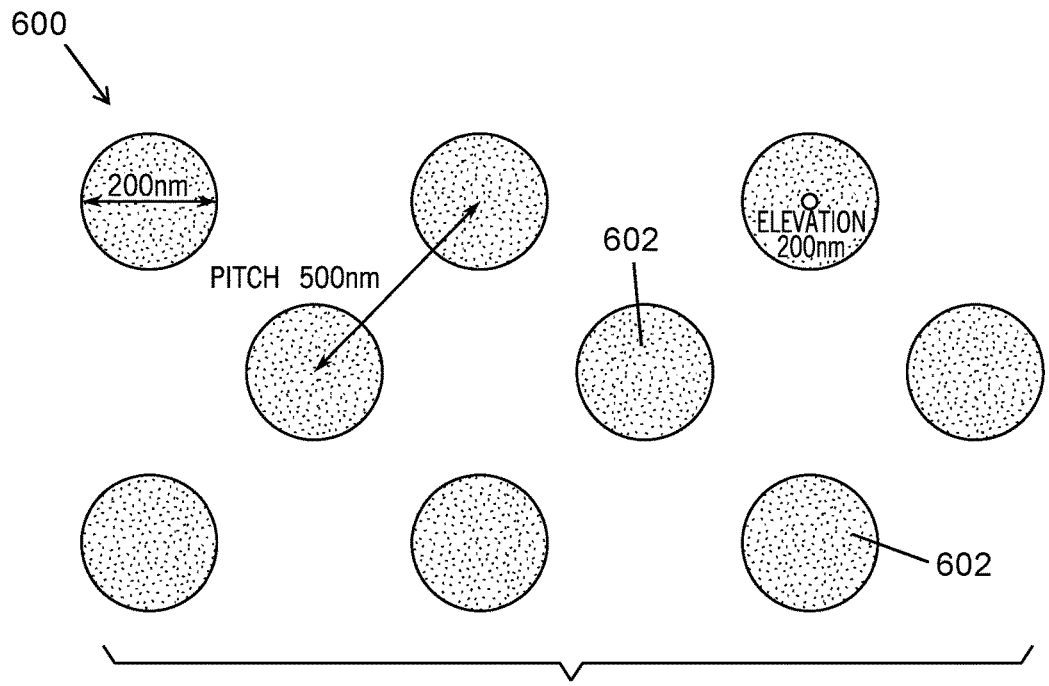
FIG. 2 depicts a plan view of an example array of reaction sites where all reaction sites are at a common elevation.
Figure 3:
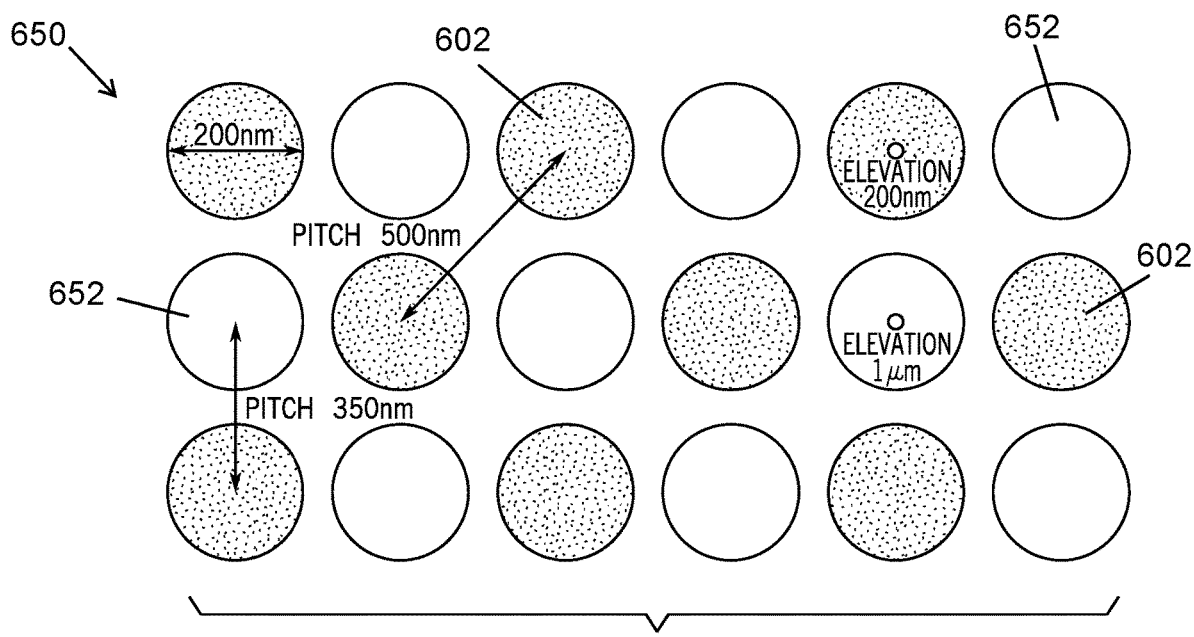
FIG. 3 depicts a plan view of an example a first array of reaction sites, where the reaction sites of the first array are at a first common elevation; and a second array of reaction sites, where the reaction sites of the second array are at a second common elevation.

The increase in packing density afforded by offset reaction site elevations is illustrated in FIGS. 2-3. FIG. 2 shows an arrangement 600 where reaction sites 602 are all located at a common z-plane (i.e., depth or elevation) and resolvable in the x-y dimension using commercially available optics. In this example, reaction sites 602 are all at a depth or elevation of 200 nm; and are separated from each other by a pitch distance (i.e., the distance between the center of one reaction site 602 and the center of each adjacent reaction site 602) of 500 nm. Each reaction site 602 of this example is circular in shape, with a diameter of 200 nm. Increasing the packing or density of reaction sites 602, such that the pitch distances are reduced, may challenge the ability of some conventional image processing components and techniques to achieve desirable resolution of the reactions occurring at reaction sites 602. However, in some analytical applications, such as nucleic acid sequencing or other nucleic acid detection techniques, it may be desirable to increase the number of analytes in an array to maximize the throughput of analysis in view of time required to fluidically process analytical arrays and to minimize costs given the cost of reagents used to process analytical arrays.

The configuration of the arrangement 650 of FIG. 3 may provide the advantages of increased throughput and decreased costs for fluidic manipulations of the arrangement 650 while avoiding detection limitations that might plague other attempts to increase reaction site array density. In the example shown in FIG. 3, reaction sites 602, 652 are provided in two different arrays located at two different respective z-planes. In particular, reaction sites 602 are positioned at a depth or elevation of 200 nm; while reaction sites 652 positioned at a depth or elevation of 1 µm. In this arrangement 650, reaction sites 602, 652 that would otherwise neighbor each other (i.e., if located in the same z-plane) are distinguishable by altering depth of detection. Even more specifically, reaction sites 602, 652 in the combined array that are separated by about 350 nm (in the x and y directions), and that might otherwise be difficult to resolve from each other, may be distinguished by acquiring a first image by focusing an optical detector (e.g., camera system 540) at a depth of about 200 nm in this example and then acquiring a second image by focusing the optical detector (e.g., camera system 540) to a depth of about 1 µm in this example, and then removing illumination from out of focus reaction sites from those images using processing techniques such as described in more detail below. The foregoing examples of depths and pitch distances are just illustrative examples and are not intended to be limiting in any way. As another illustrative example, reaction sites 602, 652 may be separated by elevations that are within 1 to 10 times the depth of field of an objective lens such as objective lens 542.

Figure 4:
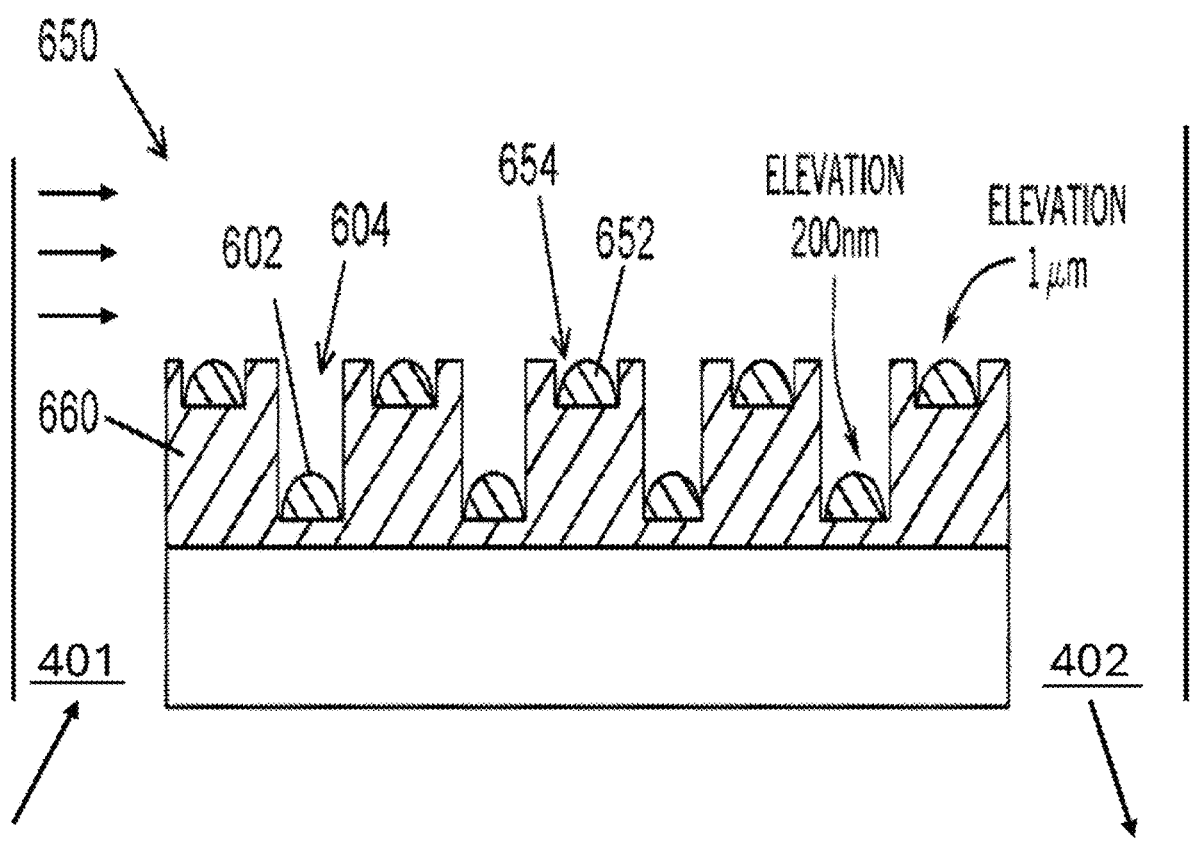
FIG. 4 depicts a cross-sectional view of an example of a flow cell providing the arrays of FIG. 3.

FIG. 4 shows an example of how the arrangement 650 of FIG. 3 may be provided by a flow cell 660 having a fluid inlet port 401 and a fluid outlet port 402. In this example, flow cell 660 defines a first array of wells 604 having a first depth; and a second array of wells 654 having a second depth. Reaction sites 602 are positioned at the bottom of wells 604, such that the first depth of wells 604 provides reaction sites 602 at the first elevation of 200 nm. Reaction sites 652 are positioned at the bottom of wells 654, such that the second depth of wells 654 provides reaction sites 652 at the second elevation of 1 µm. While wells 604, 654 are used to provide the different elevations for reaction sites 602, 652, a flow cell 660 may include other kinds of structures to provide different elevations for reaction sites. For instance, reaction sites may be positioned atop posts that extend to different respective heights. As another variation, a flow cell may provide a combination of posts and wells. In some such variations, a first set of reaction sites are positioned atop the posts while a second set of reaction sites are positioned at the bottom of the wells, such that the posts and wells provide different respective elevations for the first and second reaction sites.

As yet another variation, a flow cell may provide a set of posts where reaction sites are located at different corresponding positions along the height of each post. In such versions, the different reaction sites on each post may be separated from each other vertically (i.e., along the z-dimension) without being separated from each other horizontally (i.e., along the x-y plane). By way of example only, such an arrangement may be provided in accordance with at least some of the teachings of U.S. Provisional Pat. App. No. 63/195,123, "Flow Cells and Methods," filed May 31, 2021, the disclosure of which is incorporated by reference herein, in its entirety; and/or U.S. Pat. Pub. No. 2017/0274374, entitled "Multi-Plane Microarrays," published Sep. 28, 2017, the disclosure of which is incorporated by reference herein, in its entirety. It should therefore be understood that providing reaction sites at different elevations does not necessarily require such reaction sites to be separated from each other along a horizontal plane. Any other suitable structural configurations may be used to provide different elevations to different reaction sites.

In arrangements such as arrangement 650, resolution of reaction sites 602, 652 may be achieved via both z-plane focus of detection and differential z-plane excitation. For example, in a case where differential z-plane excitation is used to provide resolution of reaction sites 602, 652, epi-excitation may be combined with total internal reflection (TIR) excitation. Similarly, epi-excitation can be combined with excitation by other waveguides. For instance, a waveguide may contact the deep wells 604 of reaction sites 602 but not the shallow wells 654 of reaction sites 652. Illumination via the waveguide may selectively excite fluorophores within the deep wells 604 and corresponding emission may be collected from only the deep wells 604. Emission from fluorophores within the shallow wells 654 may be obtained by a subtractive method. Specifically, all wells 604, 654 may be excited by epi-illumination, and the emission from fluorophores within the shallow 654 wells may be identified by subtracting out the emission that was obtained from waveguide illumination of the deep wells 604. Other examples of how images (or other optical data) may be captured and processed from reaction sites at different elevations will be described in greater detail below.

The elevations of 200 nm and 1 µm provided above are only illustrative examples. Any other suitable elevations may be used for reaction sites 602, 652. Similarly, the reaction site size of a 200 nm diameter is only an illustrative example. Any other suitable reaction site size may be used; and a reaction site need not necessarily be circular (e.g., may instead be hexagonal or have any other suitable shape). The 500 nm pitch distance described above is also only an illustrative example. As another illustrative example, the pitch distance between reaction sites 602 may be 565 µm, the pitch distance between reaction sites 652 may be 565 µm, and the pitch distance between each reaction site 602 and the adjacent reaction sites 652 may be approximately 400 µm. Alternatively, any other suitable pitch distances may be used.

Figure 5:
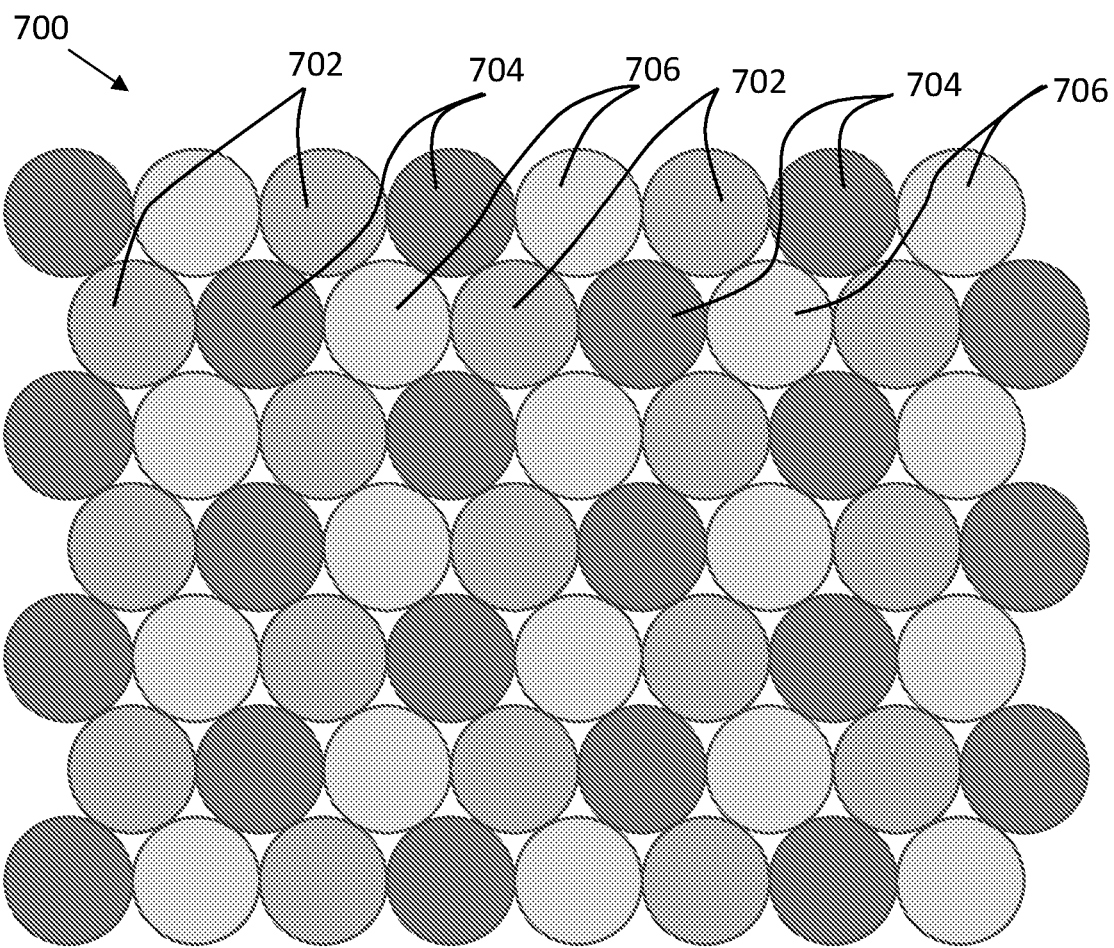
FIG. 5 depicts a plan view of an example of an arrangement of three arrays of reaction sites, with each array being at different respective elevations.
Figure 6:
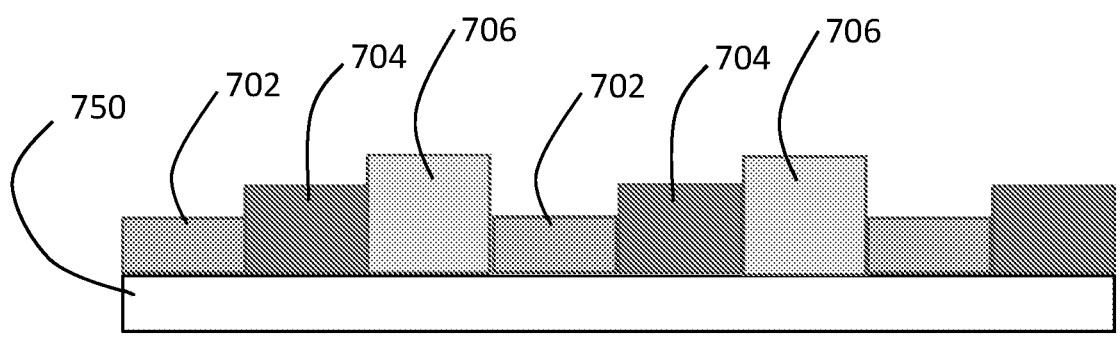
FIG. 6 depicts a cross-sectional view of an example of a flow cell providing the arrays of FIG. 5.

While the foregoing example only provides two different reaction site 602, 652 elevations, flow cells may alternatively be configured to provide reaction sites at three or more different elevations in any other suitable arrangements. For instance, FIG. 5 depicts an arrangement 700 with a first array of reaction sites 702, a second array of reaction sites 704, and a third array of reaction sites 706. Reaction sites 702 are all at a first elevation, reaction sites 704 are all at a second elevation, and reaction sites 706 are all at a third elevation. FIG. 6 depicts an example of a flow cell 750 providing reaction sites 702, 704, 706 at their different respective elevations. In some versions, flow cell 750 defines wells at different depths corresponding to the different respective elevations of reaction sites 702, 704, 706, such that reaction sites 702, 704, 706 are positioned at the bottoms of respective wells. Alternatively, a flow cell may provide reaction sites 702, 704, 706 at different respective elevations in any other suitable fashion.

Figure 7:
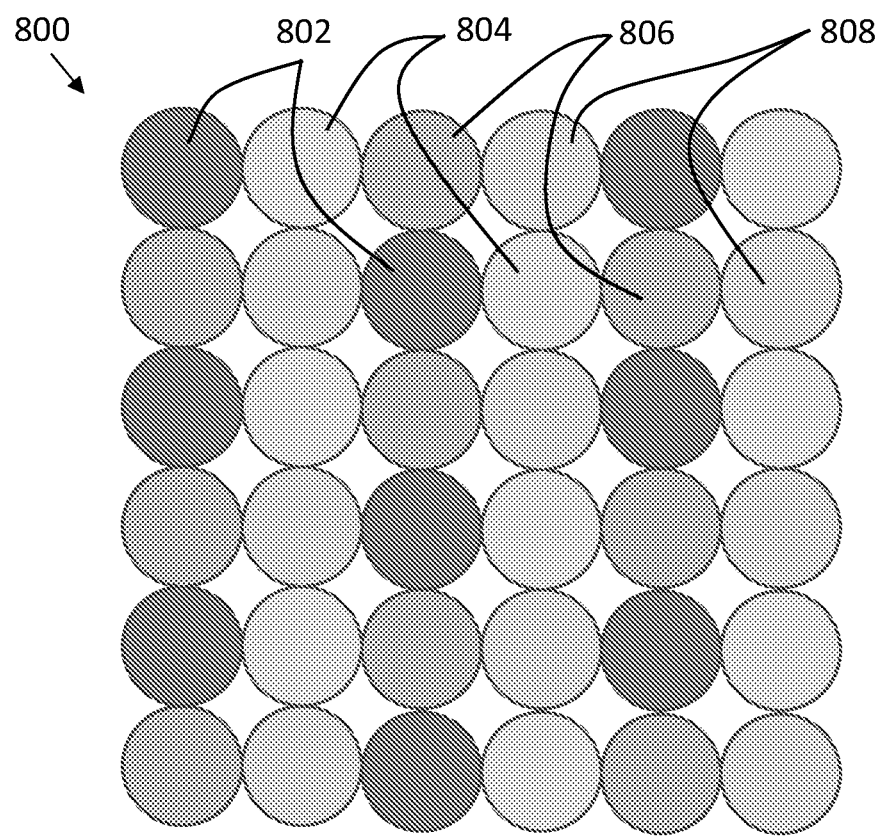
FIG. 7 depicts a plan view of an example of an arrangement of four arrays of reaction sites, with each array being at different respective elevations.
Figure 8:
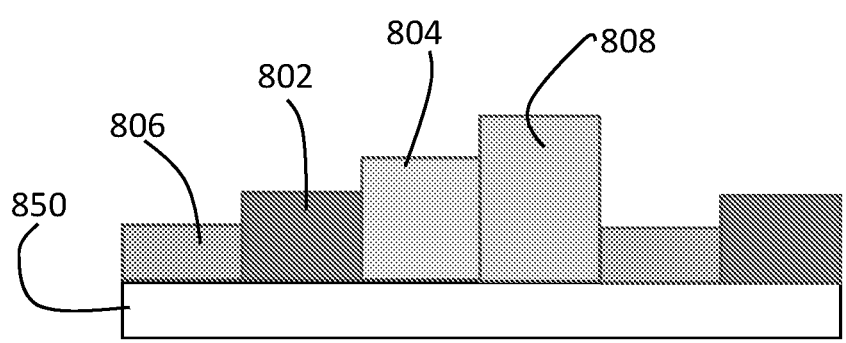
FIG. 8 depicts a cross-sectional view of an example of a flow cell providing the arrays of FIG. 7.

FIG. 7 depicts an arrangement 800 with a first array of reaction sites 802, a second array of reaction sites 804, a third array of reaction sites 806, and a fourth array of reaction sites 808. Reaction sites 802 are all at a first elevation, reaction sites 804 are all at a second elevation, reaction sites 806 are all at a third elevation, and reaction sites 808 are all at a fourth elevation. FIG. 8 depicts an example of a flow cell 850 providing reaction sites 802, 804, 806, 808 at their different respective elevations. In some versions, flow cell 850 defines wells at different depths corresponding to the different respective elevations of reaction sites 802, 804, 806, 808, such that reaction sites 802, 804, 806, 808 are positioned at the bottoms of respective wells. Alternatively, a flow cell may provide reaction sites 802, 804, 806, 808 at different respective elevations in any

III. Examples of Alternative Optical Arrangements for Flow Cells with Multi-Elevation Reaction Site Arrangement In scenarios where reaction sites are imaged via image sensors positioned over the reaction sites (e.g., similar to the system 500 shown in FIG. 1), it may be desirable to provide an imaging assembly that is configured to optically account for reaction sites being at different elevations. The following description provides several examples of imaging assembly configurations that may appropriately account for reaction sites in a flow cell being positioned at different elevations.

Figure 9A:
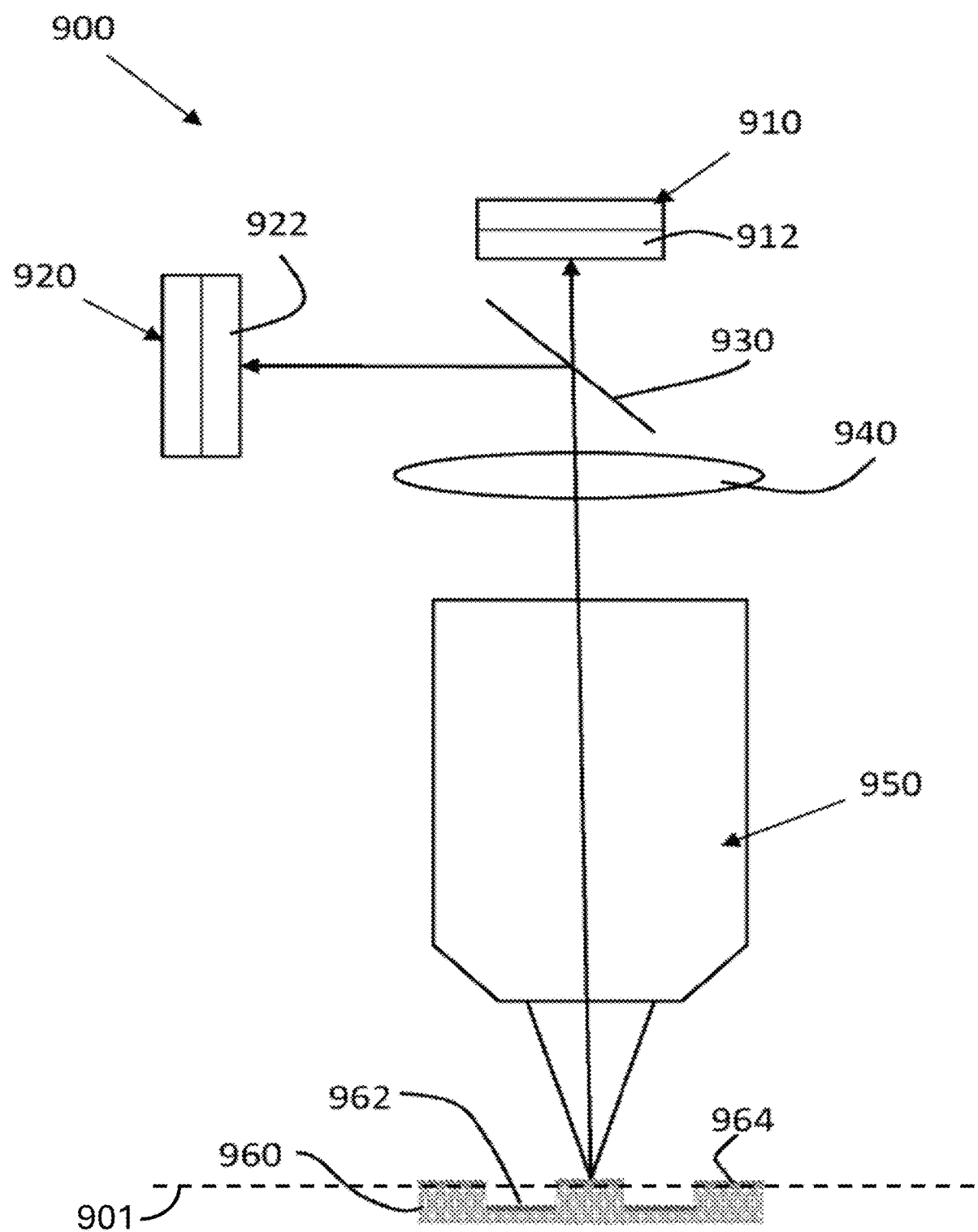
FIG. 9A depicts a schematic view of an example of an imaging assembly capturing an image of a flow cell, with the flow cell in a first position.
Figure 9B:
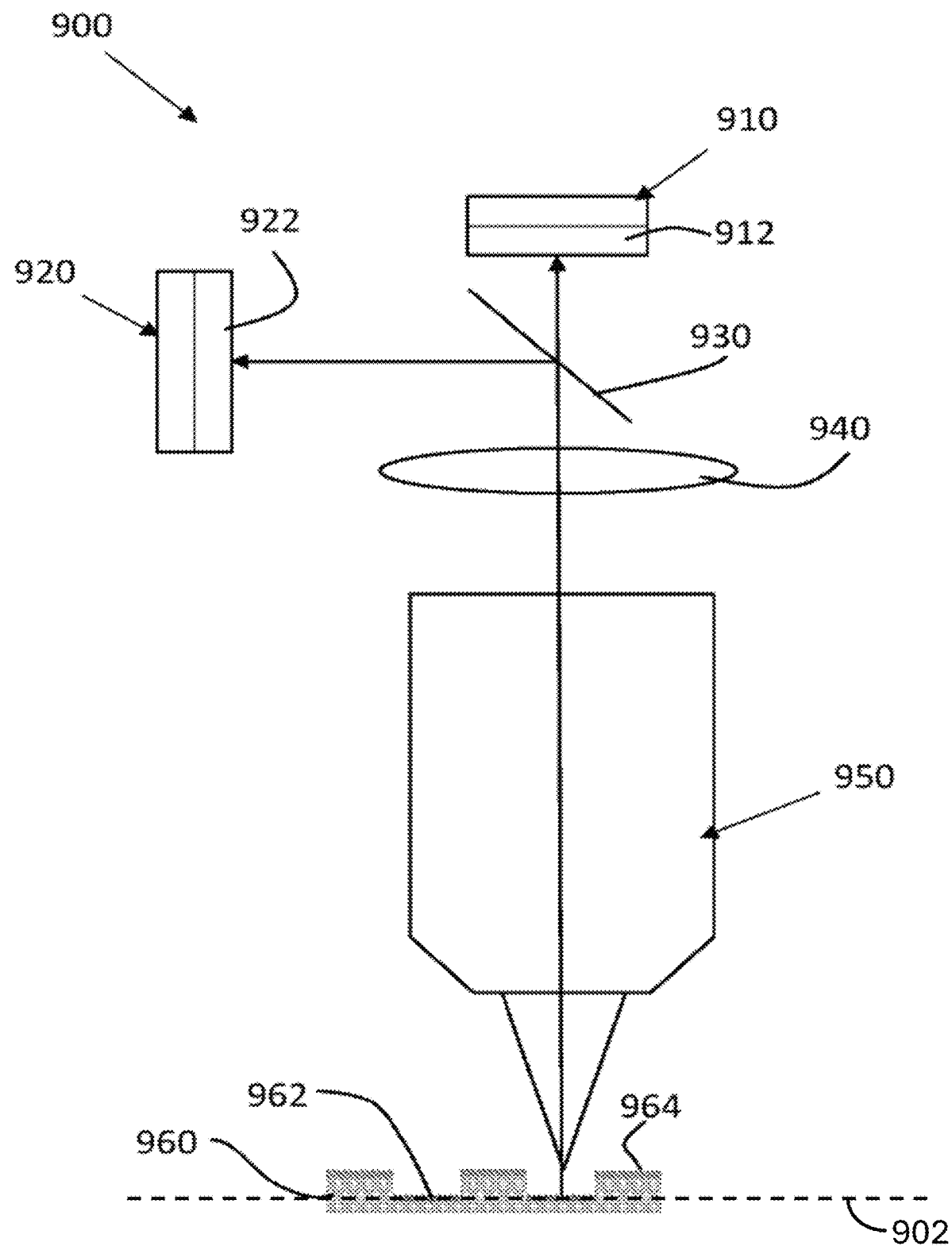
FIG. 9B depicts a schematic view of the imaging assembly of FIG. 9A capturing another image of the flow cell, with the flow cell in a second position.

FIGS. 9A-9B show an imaging assembly 900 that includes a first camera 910, a second camera 920, a beam splitter 930, a tube lens 940, and an objective lens assembly 950. First camera 910 includes a first image sensor 912. Second camera 920 includes a second image sensor 922. Beam splitter 930 is configured to split images that are passed through tube lens 940 such that the images reach both cameras 910, 920 despite cameras 910, 920 being positioned separately and orthogonally relative to each other. Imaging assembly 900 is positioned over a flow cell 960 that includes reaction sites 962, 964. A light source (not shown) is used to emit an excitation light toward reaction sites 962, 964. Fluorophores at reaction sites 962, 964 emit light in response to the excitation light from the light source. Objective lens assembly 950 is configured to capture and collimate these light emissions from reaction sites 962, 964. Tube lens 940 is configured to re-image the emitted light from objective lens assembly 950 onto image sensors 912, 922, with a magnification determined by the ratio of the focal lengths.

In this example, reaction sites 962 are all positioned at a first elevation while reaction sites 964 are all positioned at a second elevation, with the second elevation being higher than the first elevation. While flow cell 960 only provides two different reaction site 962, 964 elevations in this example, other versions may provide three or more reaction site elevations.

During an example of an image capture process, imaging assembly 900 may capture a sequence of images as flow cell 960 is moved along the x-y plane. For instance, imaging assembly 900 may capture a first image of flow cell 960 when a reaction site 964 is positioned directly under imaging assembly 900 as shown in FIG. 9A; then capture a second image of flow cell 960 when a reaction site 962 is positioned directly under imaging assembly 900 as shown in FIG. 9B. In some variations, flow cell 960 is moved relative to imaging assembly 900 to capture a sequence of images (e.g., using a component similar to focus component 575 described above). In some other versions, imaging assembly 900 is moved relative to flow cell 960 using any suitable components.

In either case, first camera 910 may be focused such that the focal plane (first focal plane 901) of first camera 910 is positioned at the elevation of reaction sites 962, such that first camera 910 is used to capture images in which reaction sites 962 are in focus and other reaction sites (e.g., reaction sites 964) are out of focus. Second camera 920 may be focused such that the focal plane (second focal plane 902) of second camera 920 is positioned at the elevation of reaction sites 964, such that second camera 920 is used to capture images in which reaction sites 964 are in focus and other reaction sites (e.g., reaction sites 962) are out of focus. Thus, at the operational stage shown in FIG. 9A, reaction site 964 may be imaged sharply by camera 920 while reaction site 962 is out of focus. At the operational stage shown in FIG. 9B, reaction site 962 may be imaged sharply by camera 910 while reaction site 964 is out of focus.

Figure 13A:
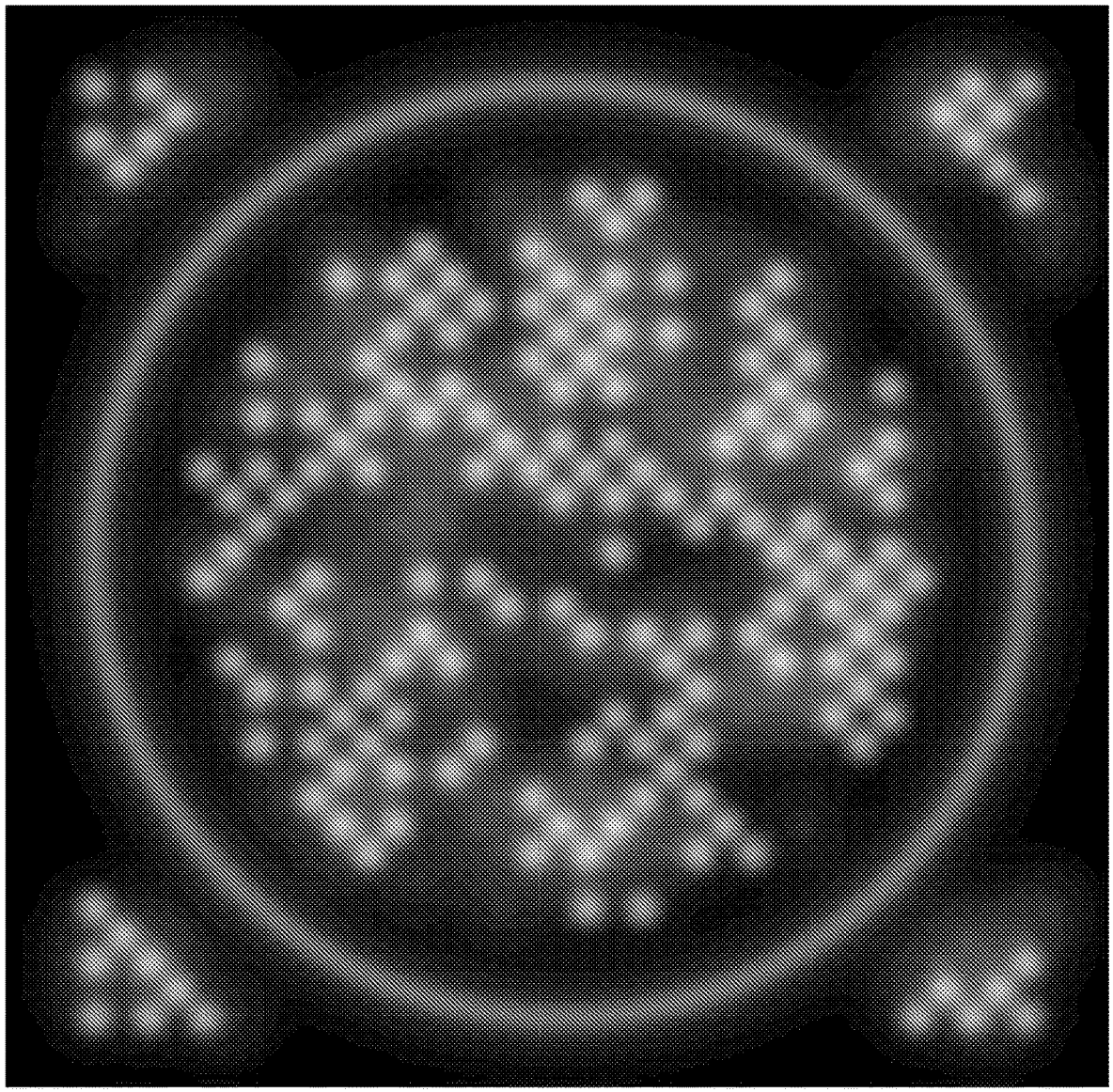
FIG. 13A depicts an exemplary image including illumination from reaction sites at different elevations.
Figure 13B:
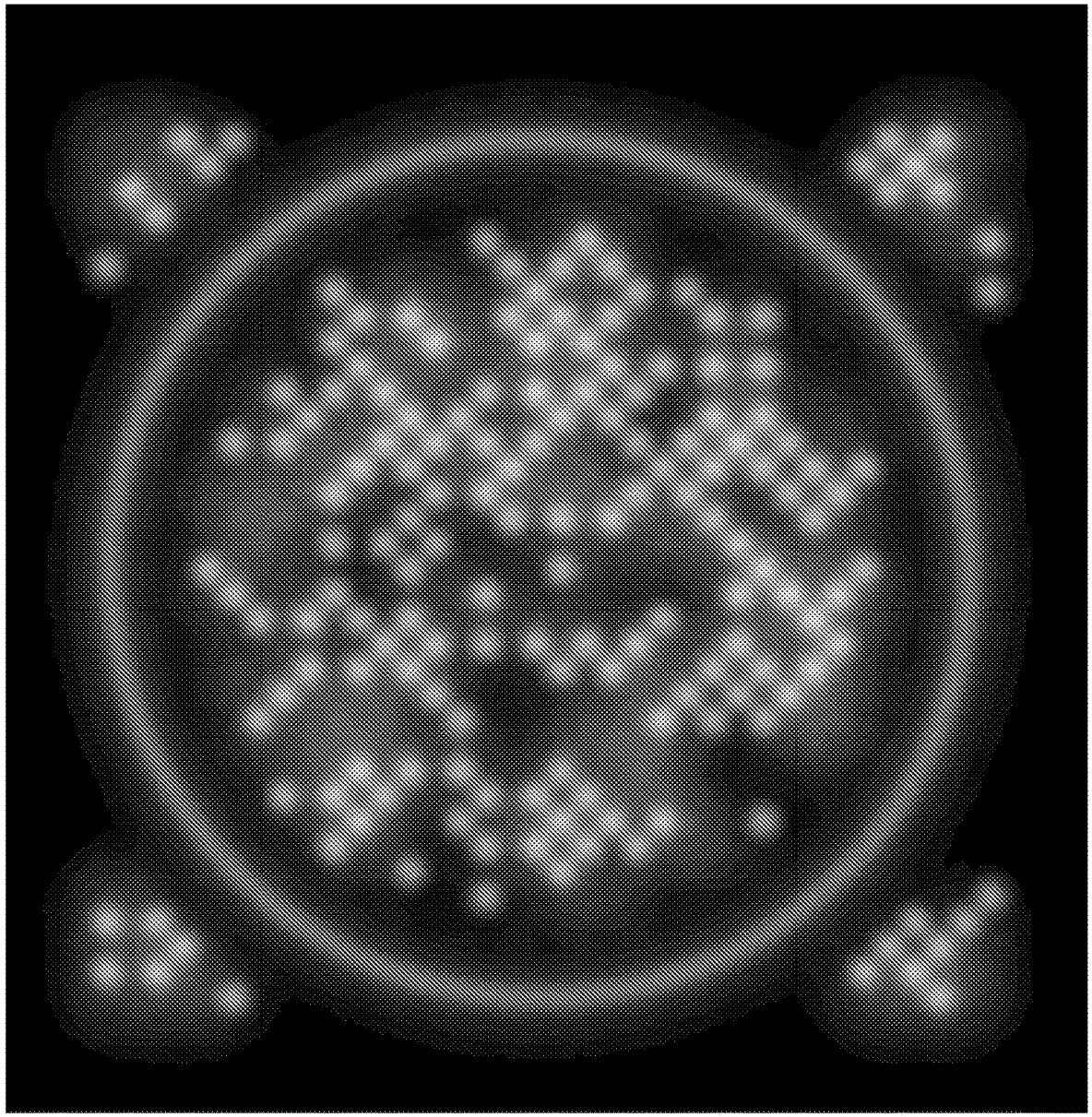
FIG. 13B depicts an exemplary image including illumination from reaction sites at different elevations.
Figure 14A:
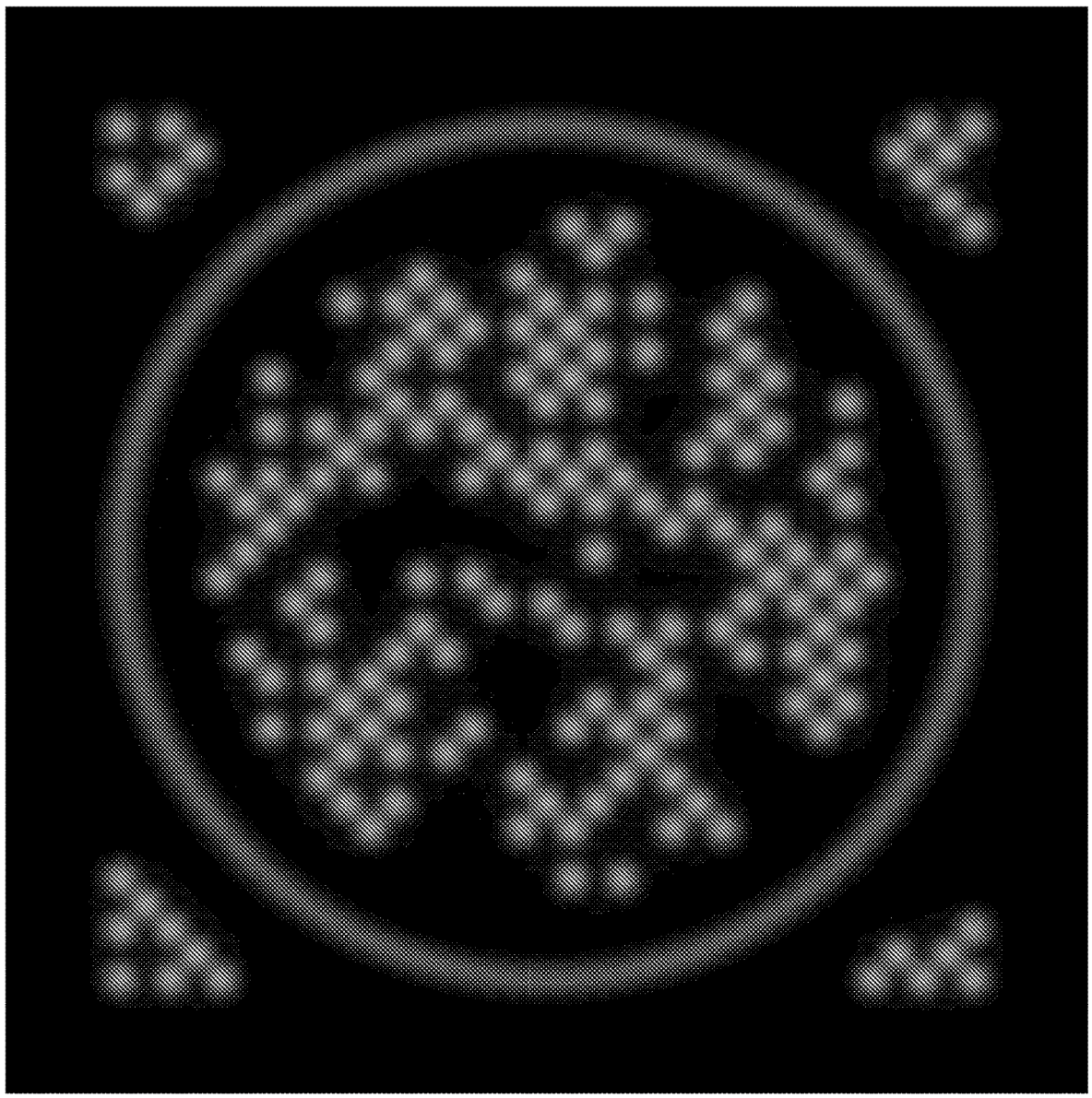
FIG. 14A depicts an exemplary image including illumination from in focus reaction sites after removal of background illumination.
Figure 14B:
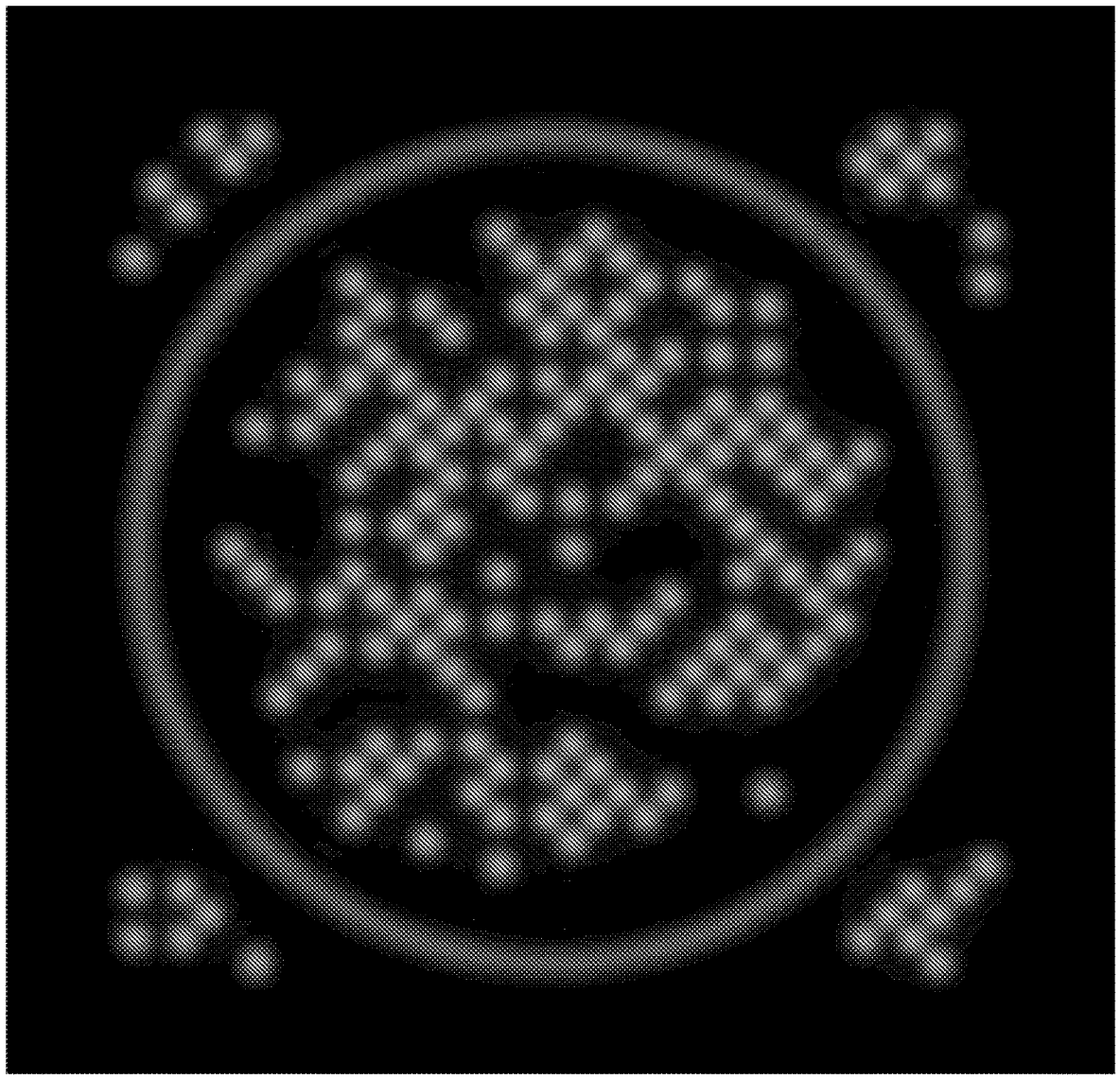
FIG. 14B depicts an exemplary image including illumination from in focus reaction sites after removal of background illumination.
Figure 15:
FIG. 15 depicts an exemplary image combining illumination from different in focus reaction sites in underlying images.

FIGS. 13A-13B show exemplary images which may be generated in this manner. FIG. 13A shows an image in which reaction sites 962 at a first elevation are in focus, while reaction sites 964 at a second elevation are out of focus. FIG. 13B shows a companion image, in which reaction sites 962 at the first elevation are out of focus, while reaction sites 964 at the second elevation are in focus. As set forth herein, the background illumination from the out of focus reaction sites may be removed from images such as shown in FIGS. 13A-13B, thereby providing images such as shown in FIGS. 14A-14B. In those images, FIG. 14A illustrates signals from the in focus reaction sites 962 of FIG. 13A after background signals from out of focus reaction sites 964 have been removed, while FIG. 14B illustrates signals from the in focus reaction sites 964 of FIG. 13B after background signals from out of focus reaction sites 962 of FIG. 13B have been removed. Images such as shown in FIGS. 14A-14B may then be processed (e.g., by providing data used for sequencing by synthesis) and/or they may be combined to form a single super-resolution image such as shown in FIG. 15, which may allow all individual reaction sites to be resolved even though resolving individual reaction sites may not have been possible directly (e.g., because the pitch between adjacent reaction sites may have been below the diffraction limit of emitted light). Such processing may be executed by a controller such as controller 104, 595 and/or using any other suitable components.

While the foregoing example describes relative movement between flow cell 960 and imaging assembly 900 during image capture, some variations may provide a stationary relationship between flow cell 960 and imaging assembly 900. In some such variations, first camera 910 may capture images of one or more reaction sites 962 while second camera 920 simultaneously captures images of one or more reaction sites 964. Even in variations where first camera 910 captures images of one or more reaction sites 962 while second camera 920 simultaneously captures images of one or more reaction sites 964, there may still be some relative movement flow cell 960 and imaging assembly 900 during image capture. For instance, in one stage of operation first camera 910 may capture images of a first batch of more reaction sites 962 while second camera 920 simultaneously captures images of a first batch of reaction sites 964. Then, flow cell 960 may be moved relative to imaging assembly 900 such that first camera 910 may subsequently capture images of a second batch of reaction sites 962 while second camera 920 simultaneously captures images of a second batch of reaction sites 964.

Figure 10A:
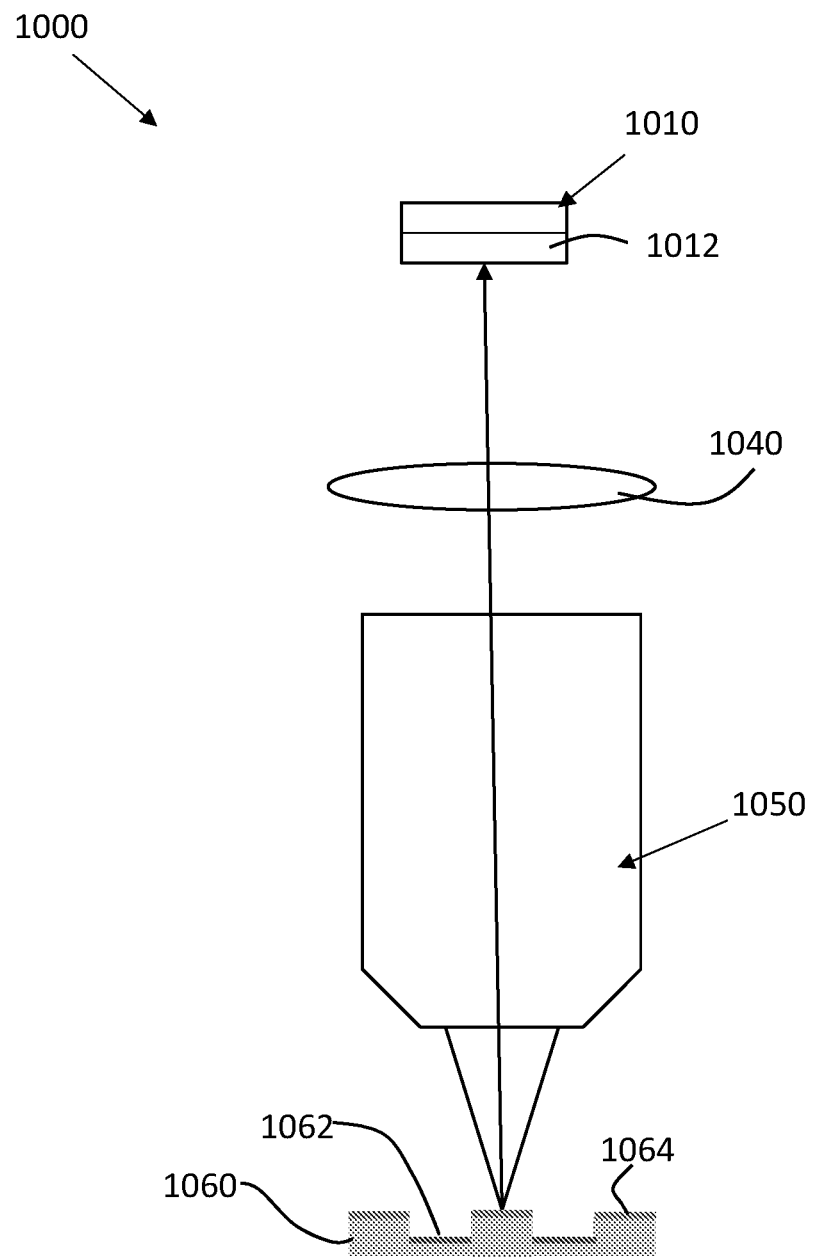
FIG. 10A depicts a schematic view of an example of another imaging assembly capturing an image of a flow cell, with the flow cell in a first position.
Figure 10B:
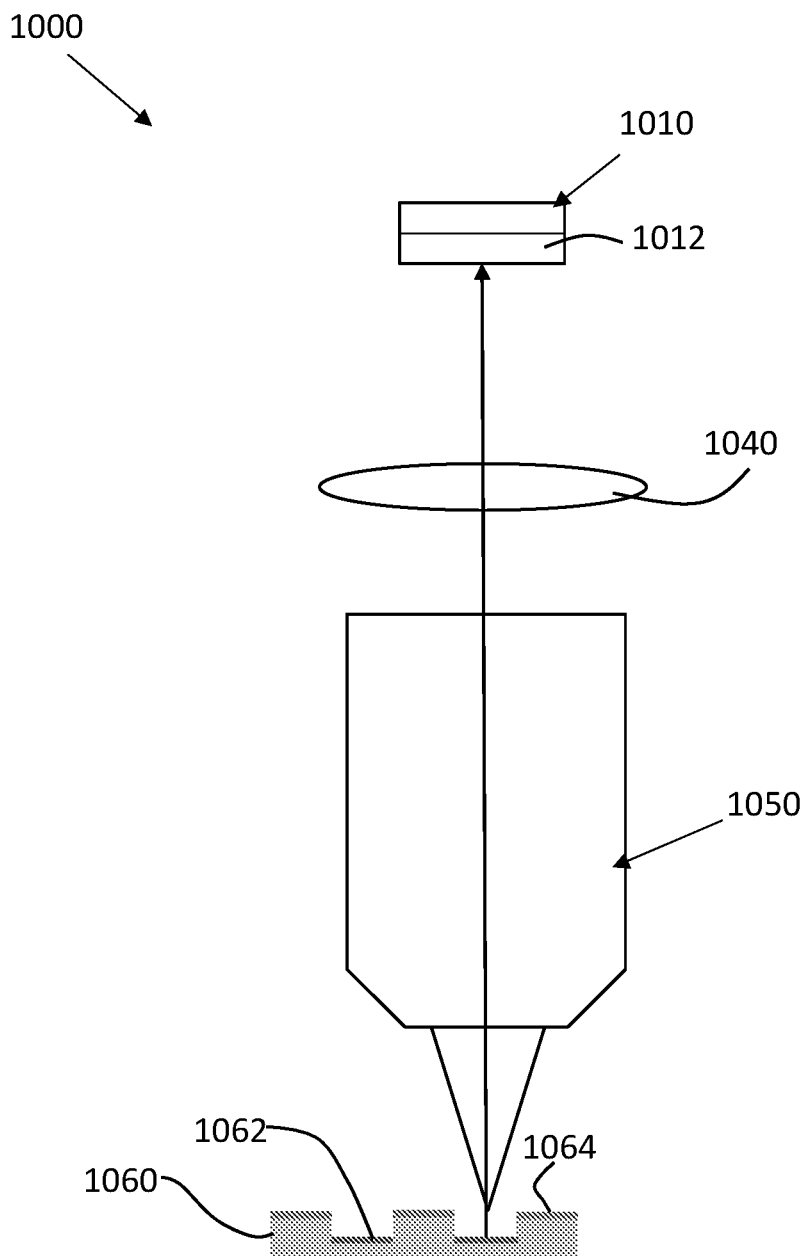
FIG. 10B depicts a schematic view of the imaging assembly of FIG. 10A capturing another image of the flow cell, with the flow cell in a second position.

FIGS. 10A-10B show an imaging assembly 1000 that includes a camera 1010, a tube lens 1040, and an objective lens assembly 1050. Camera 1010 includes an image sensor 1012. Imaging assembly 1000 is positioned over a flow cell 1060 that includes reaction sites 1062, 1064. A light source (not shown) is used to emit an excitation light toward reaction sites 1062, 1064. Fluorophores at reaction sites 1062, 1064 emit light in response to the excitation light from the light source. Objective lens assembly 1050 is configured to capture and collimate these light emissions from reaction sites 1062, 1064. Tube lens 1040 is configured to re-image the emitted light from objective lens assembly 1050 onto image sensor 1012, with a magnification determined by the ratio of the focal lengths.

In this example, reaction sites 1062 are all positioned at a first elevation while reaction sites 1064 are all positioned at a second elevation, with the second elevation being higher than the first elevation. While flow cell 1060 only provides two different reaction site 1062, 1064 elevations in this example, other versions may provide three or more reaction site elevations.

During an example of an image capture process, imaging assembly 1000 may capture a sequence of images as flow cell 1060 is moved along the x-y plane. For instance, imaging assembly 1000 may capture a first image of flow cell 1060 when a reaction site 1064 is positioned directly under imaging assembly 1000 as shown in FIG. 10A; then capture a second image of flow cell 1060 when a reaction site 1062 is positioned directly under imaging assembly 1000 as shown in FIG. 10B. In some variations, flow cell 1060 is moved relative to imaging assembly 1000 to capture a sequence of images (e.g., using a component similar to focus component 575 described above). In some other versions, at least a portion of imaging assembly 1000 is moved relative to flow cell 1060 using any suitable components. In either case, imaging assembly 1000 may provide selective refocusing of camera 1010 based on the position of flow cell 1060 in relation to imaging assembly 1000. Such selective refocusing of camera 1010 may be provided by varying the vertical position of objective lens assembly 1050 relative to flow cell 1060 and image sensor 1012, with the vertical position of objective lens assembly 1050 being based on the position of flow cell 1060 along a horizontal plane.

At operational stages such as those shown in FIG. 10A, camera 1010 may be automatically focused such that the focal plane of camera 1010 is positioned at the elevation of reaction sites 1064, such that camera 1010 is used to capture images focused on reaction sites 1064 when reaction sites 1064 are positioned directly under imaging assembly 1000. At operational stages such as those shown in FIG. 10B, camera 1010 may be automatically focused such that the focal plane of camera 1010 is positioned at the elevation of reaction sites 1062, such that camera 1010 is used to capture images focused on reaction sites 1062 when reaction sites 1062 are positioned directly under imaging assembly 1000. Subsequently, each image captured when a reaction site 1064 at a first elevation was in focus may be correlated with an image captured when a reaction site 1062 at a second elevation was captured and, to the extent those images are offset relative to each other, one or both of those images may be translated so that they would be co-registered and could be used for removing background illumination from each other as described in more detail below. Any suitable components and techniques may be used to synchronize the focusing of camera 1010 with the positioning of flow cell 1060. The images captured by camera 1010 may be processed in accordance with the teachings herein. Such processing may be executed by a controller such as controller 104, 595 and/or using any other suitable components.

Figure 11A:
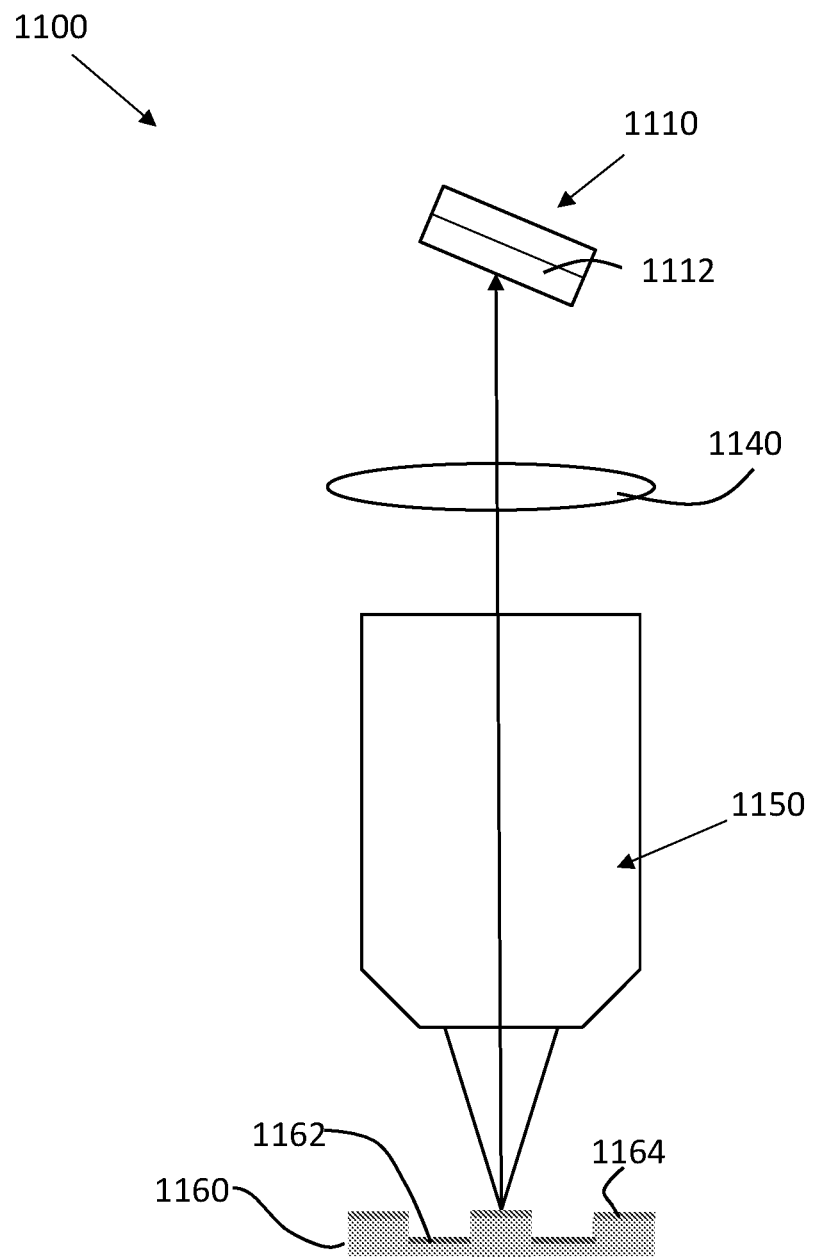
FIG. 11A depicts a schematic view of an example of another imaging assembly capturing an image of a flow cell, with the flow cell in a first position.
Figure 11B:
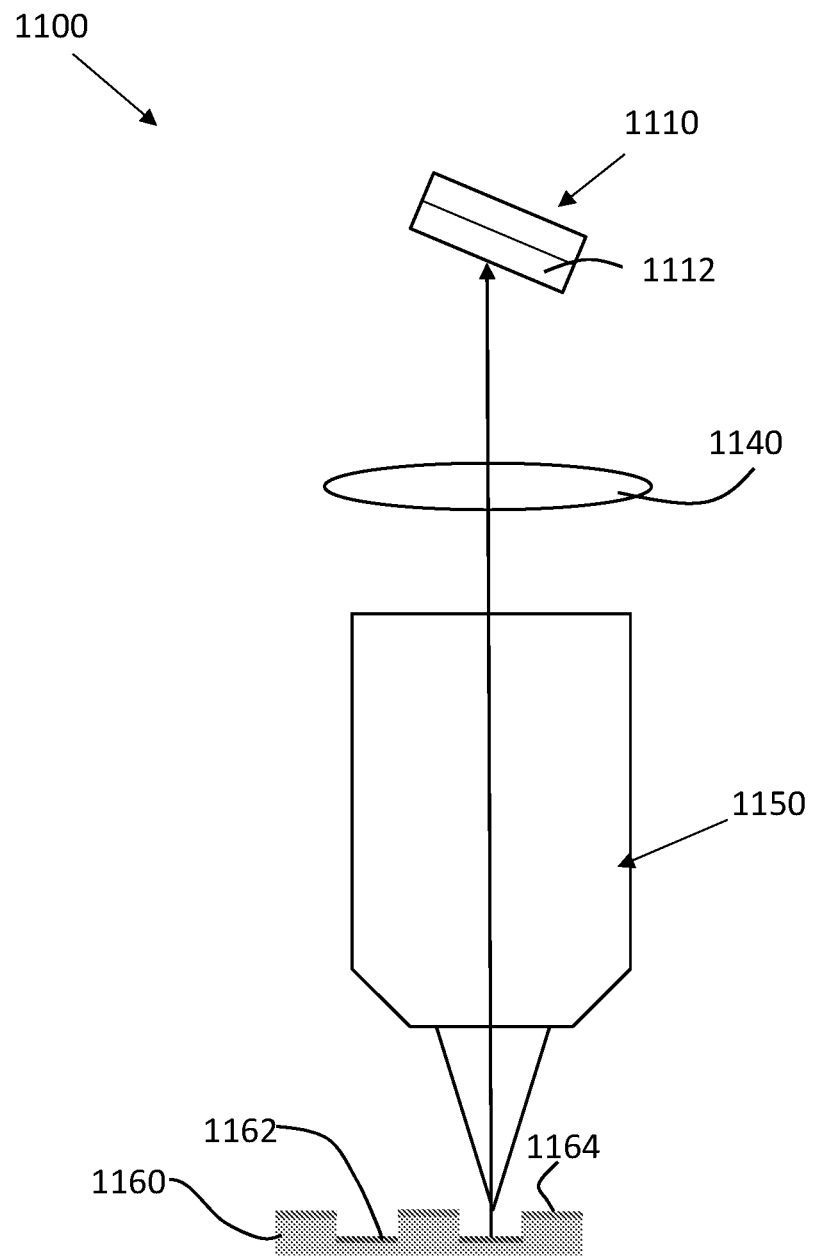
FIG. 11B depicts a schematic view of the imaging assembly of FIG. 11A capturing another image of the flow cell, with the flow cell in a second position.

FIGS. 11A-11B show an imaging assembly 1100 that includes a camera 1110, a tube lens 1140, and an objective lens assembly 1150. Camera 1110 includes an image sensor 1112. Imaging assembly 1100 is positioned over a flow cell 1160 that includes reaction sites 1162, 1164. A light source (not shown) is used to emit an excitation light toward reaction sites 1162, 1164. Fluorophores at reaction sites 1162, 1164 emit light in response to the excitation light from the light source. Objective lens assembly 1150 is configured to capture and collimate these light emissions from reaction sites 1162, 1164. Tube lens 1140 is configured to re-image the emitted light from objective lens assembly 1150 onto image sensor 1112, with a magnification determined by the ratio of the focal lengths.

Unlike camera 1010 of imaging assembly 1000 described above, camera 1110 of imaging assembly 1100 is oriented obliquely relative to flow cell 1160, such that image sensor 1112 is not parallel with reaction sites 1162, 1164. In this example, reaction sites 1162 are all positioned at a first elevation while reaction sites 1164 are all positioned at a second elevation, with the second elevation being higher than the first elevation. While flow cell 1160 only provides two different reaction site 1162, 1164 elevations in this example, other versions may provide three or more reaction site elevations.

During an example of an image capture process, imaging assembly 1100 may capture a sequence of images as flow cell 1160 is moved along the x-y plane. For instance, imaging assembly 1100 may capture a first image of flow cell 1160 when a reaction site 1164 is positioned directly under imaging assembly 1100 as shown in FIG. 11A; then capture a second image of flow cell 1160 when a reaction site 1162 is positioned directly under imaging assembly 1100 as shown in FIG. 11B. In some variations, flow cell 1160 is moved relative to imaging assembly 1100 to capture a sequence of images (e.g., using a component similar to focus component 575 described above). In some other versions, imaging assembly 1100 is moved relative to flow cell 1160 using any suitable components.

Unlike imaging assembly 1000 of FIGS. 10A-10B, imaging assembly 1100 of FIGS. 11A-11B need not necessarily provide refocusing of camera 1110 based on the position of flow cell 1160 in relation to imaging assembly 1100. This is because camera 1110 is oriented obliquely relative to flow cell 1160, such that image sensor 1112 is not parallel with reaction sites 1162, 1164. Due to this oblique orientation of camera 1110, certain regions of images captured by camera 1110 will be substantially in focus while other regions of images captured by camera 1110 will not be substantially in focus, with the level of focus being dependent on the distance of the captured subject matter from the camera. In other words, the oblique tilt angle of camera 1110 may be selected such that at least some regions of reaction sites 1162, 1164 will be in focus regardless of the position of flow cell 1160 along the x-y plane.

For instance, at operational stages such as those shown in FIG. 11A, only a first region of a reaction site 1164 will be substantially in focus in an image captured by camera 1110 while only a first region of reaction site 1164 will be substantially in focus in an image captured by camera 1110. At operational stages such as those shown in FIG. 11B, only a second region of a reaction site 1164 will be substantially in focus in an image captured by camera 1110 while only a second region of reaction site 1164 will be substantially in focus in an image captured by camera 1110.

Two or more images may be captured of each reaction site 1162, 1164 as flow cell 1160 moves along the x-y plane, to thereby ensure that more than one region of each reaction site 1162, 1164 is substantially in focus among the images in an image set. Thus, as flow cell 1160 moves along the x-y plane, camera 1110 may capture a series of images where, among the images in the series, all regions of each reaction site 1162, 1164 are substantially in focus, with the region of focus for each reaction site 1162, 1164 varying based on the x-y position of flow cell 1160 when the image at hand was captured. Image processing techniques may be used to merge the substantially in-focus regions of the various images of each reaction site 1162, 1164 to create a composite image of each reaction site 1162, 1164, where the entire composite image of each reaction site 1162, 1164 is substantially in focus. To the extent such composite images of reaction sites 1162 are offset relative to composite images of reaction sites 1164, one or both of those composite images may be translated so that they would be co-registered and could be used for removing background illumination from each other as described in more detail below. The images captured by camera 1110 may be further processed in accordance with the teachings herein. Such processing may be executed by a controller such as controller 104, 595 and/or using any other suitable components.

Figure 12A:
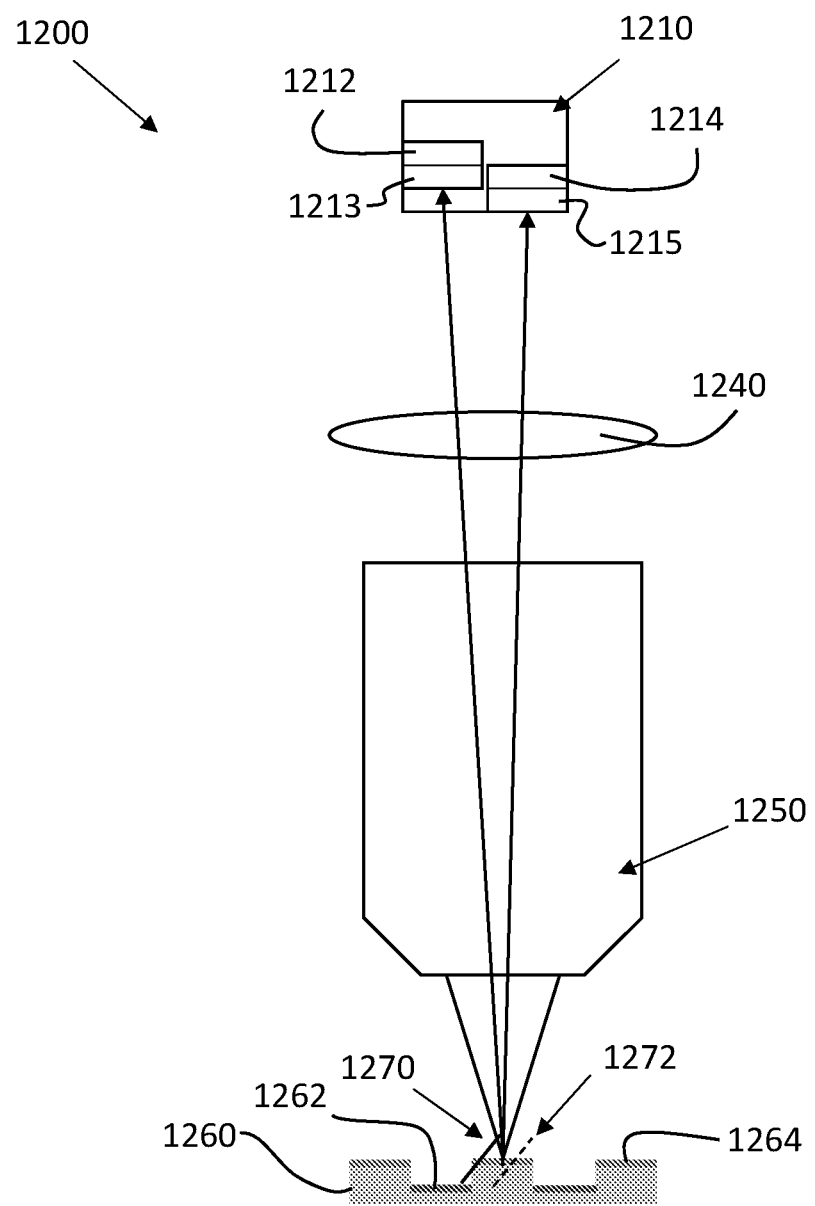
FIG. 12A depicts a schematic view of an example of another imaging assembly capturing an image of a flow cell, with the flow cell in a first position.
Figure 12B:
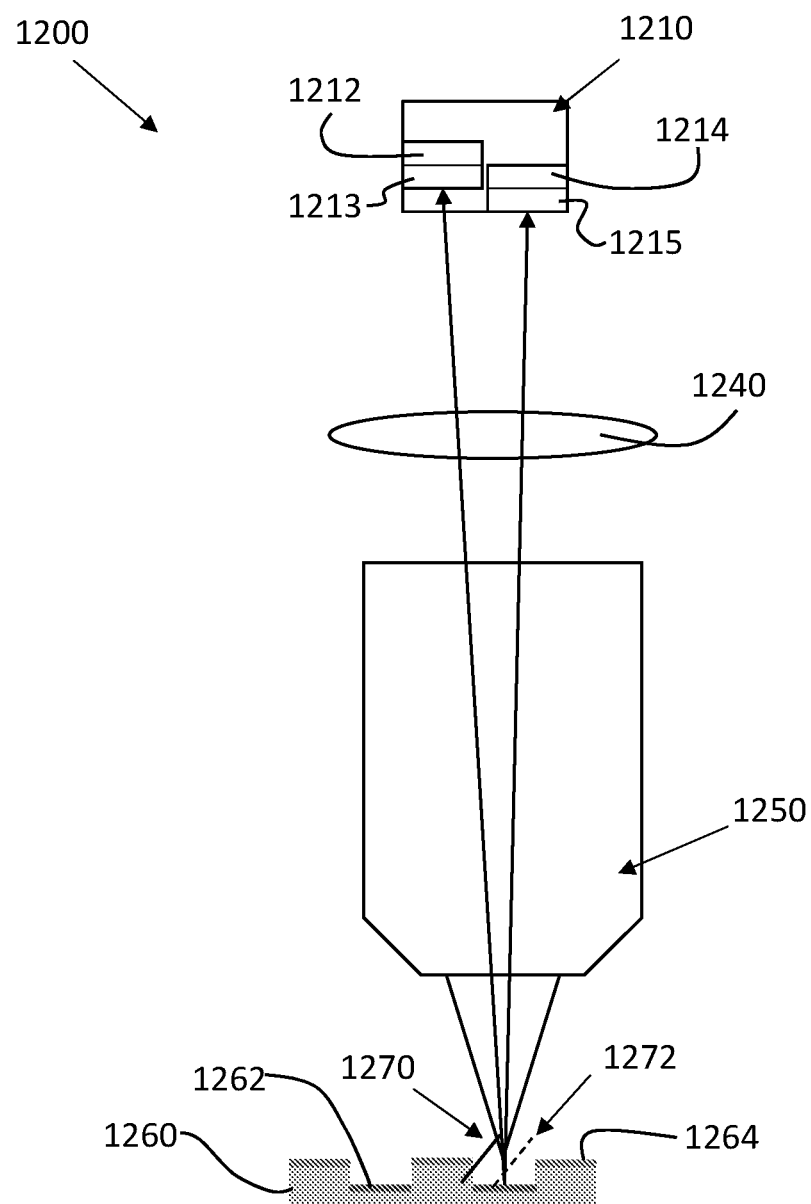
FIG. 12B depicts a schematic view of the imaging assembly of FIG. 12A capturing another image of the flow cell, with the flow cell in a second position.

FIGS. 12A-12B show an imaging assembly 1200 that includes a camera 1210, a tube lens 1240, and an objective lens assembly 1250. Camera 1210 includes a first image sensor 1212, a first bandpass filter 1213, a second image sensor 1214, and a second bandpass filter 1214. Image sensor 1212 is vertically offset relative to image sensor 1214. Imaging assembly 1200 is positioned over a flow cell 1260 that includes reaction sites 1162, 1264. In the present example, the vertical offset between image sensors 1212, 1214 is approximately equal to the vertical offset between reaction sites 1262, 1264 multiplied by the magnification squared. A light source (not shown) is used to emit an excitation light toward reaction sites 1262, 1264. Fluorophores at reaction sites 1262, 1264 emit light in response to the excitation light from the light source. Objective lens assembly 1250 is configured to capture and collimate these light emissions from reaction sites 1262, 1264. Tube lens 1240 is configured to re-image the emitted light from objective lens assembly 1250 onto image sensors 1212, 1214, with a magnification determined by the ratio of the focal lengths.

In this example, reaction sites 1262 are all positioned at a first elevation while reaction sites 1264 are all positioned at a second elevation, with the second elevation being higher than the first elevation. While flow cell 1260 only provides two different reaction site 1262, 1264 elevations in this example, other versions may provide three or more reaction site elevations.

During an example of an image capture process, imaging assembly 1200 may capture a sequence of images as flow cell 1260 is moved along the x-y plane. Moreover, imaging assembly 1200 may operate as a line scan system, such that imaging assembly 1200 may effectively capture images of relatively large areas simultaneously. For instance, with imaging assembly 1200 operating as a line scan system, imaging assembly 1200 may simultaneously capture images of reaction sites 1262 and reaction sites 1264 at the stage shown in FIG. 12A; and also simultaneously capture images of reaction sites 1262 and reaction sites 1264 at the stage shown in FIG. 12B. By enabling the capture of images of several reaction sites 1262, 1264 simultaneously, imaging assembly 1200 may provide a faster processing times than some other versions.

In some variations, flow cell 1260 is moved relative to imaging assembly 1200 to capture a sequence of images (e.g., using a component similar to focus component 575 described above). In some other versions, imaging assembly 1200 is moved relative to flow cell 1260 using any suitable components. In either case, first image sensor 1212 is vertically positioned such that the focal plane of first image sensor 1212 is positioned at the elevation of reaction sites 1264, such that first image sensor 1212 is used to capture images focusing on reaction sites 1264. Second image sensor 1214 is vertically positioned such that the focal plane of second image sensor 1214 is positioned at the elevation of reaction sites 1262, such that second image sensor 1214 is used to capture images focusing on reaction sites 1262. The images captured by image sensors 1212, 1214 may be processed in accordance with the teachings herein. Such processing may be executed by a controller such as controller 104, 595 and/or using any other suitable components.

While the foregoing example describes relative movement between flow cell 1260 and imaging assembly 1200 during image capture, some variations may provide a stationary relationship between flow cell 1260 and imaging assembly 1200. In some such variations, first image sensor 1212 may capture images focusing on one or more reaction sites 1264 while second image sensor 1214 simultaneously captures images focusing on one or more reaction sites 1262. In such scenarios, light 1270 at a first excitation wavelength may be used to illuminate reaction sites 1262. Fluorophores at reaction sites 1262 may emit light in a first emission wavelength spectrum in response to the excitation light 1270. First bandpass filter 1213 may be configured to only allow light within a certain wavelength range, that includes at least part of the first emission wavelength spectrum, to pass through first bandpass filter 1213.

Similarly, light 1272 at a second excitation wavelength may be used to illuminate reaction sites 1264. Fluorophores at reaction sites 1264 may emit light in a second emission wavelength spectrum in response to the excitation light 1272. In some implementations, the second emission wavelength spectrum can be different from the first emission wavelength spectrum. For example, the first emission wavelength spectrum may emit light from approximately 630 nm to approximately 780 nm and the second emission wavelength spectrum may emit light from approximately 530 nm to approximately 625 nm. In other implementations, the second emission wavelength spectrum can overlap part of the first emission wavelength spectrum. For example, the first emission wavelength spectrum may emit light from approximately 550 nm to approximately 700 nm and the second emission wavelength spectrum may emit light from approximately 475 nm to approximately 650 nm. Second bandpass filter 1215 may be configured to only allow light within a certain wavelength range, that includes the second emission wavelength spectrum, to pass through second bandpass filter 1215.

Even in variations where first image sensor 1212 captures images focusing on one or more reaction sites 1264 while second image sensor 1214 simultaneously captures images focusing on one or more reaction sites 1262, there may still be some relative movement flow cell 1260 and imaging assembly 1200 during image capture. For instance, in one stage of operation first image sensor 1212 may capture images of a first batch of more reaction sites 1264 while second image sensor 1214 simultaneously captures images of a first batch of reaction sites 1262. Then, flow cell 1260 may be moved relative to imaging assembly 1200 such first image sensor 1212 may capture images of a second batch of reaction sites 1264 while second image sensor 1214 simultaneously captures images of a second batch of reaction sites 1262.

IV. Resolution of Reaction Sites Based on Elevation Derived Focus Deviations As explained above, in a system in which reaction sites are set at different elevations from each other, it is possible to capture images in which signals from reaction sites at different elevations have different optical properties (e.g., being in-focus or out of focus). Using these different optical properties, it may be possible to resolve reaction sites at different elevations, thereby allowing images like those shown in FIGS. 13A-13B to be used to derive cleaned images such as shown in FIGS. 14A-14B, and ultimately to derive super-resolution images such as shown in FIG. 15 in which individual reactions are depicted in focus and resolvable from their neighbors, despite neighboring reaction sites being separated by a pitch which may be less than the diffraction limit of the light emitted from the reaction sites. Examples of processing which may be used for this purpose are provided below in the context of FIG. 16.

Figure 16:
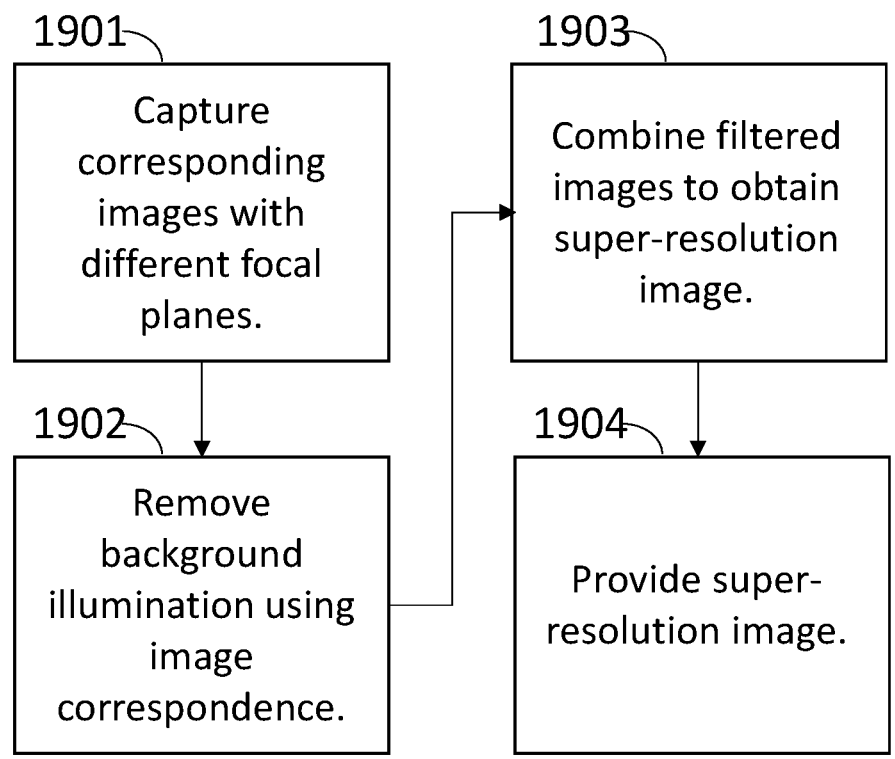
FIG. 16 depicts illustrates a process which may be used to obtain a super-resolution image of a flow cell having reaction sites at different elevations.

Turning now to FIG. 16, that figure illustrates a process which may be used to obtain a super-resolution image of a flow cell having reaction sites at two different elevations, such as that illustrated in FIGS. 3 and 4. Initially, in block 1901, corresponding images having different focal planes are captured. This may be done, for example, by simultaneously capturing images of the same portion of a flow cell with two different cameras having two different focal planes, such as using an imaging assembly 900 as shown in FIG. 9A, or an imaging assembly 1200 as such on FIG. 12A.

Next, in block 1902, the background illumination (i.e., the illumination from reaction sites to be removed from an image) is removed from each image using the correspondence between the images captured in block 1901. This may be done, for example, through use of equations 1 and 2:

$$I_1 = F^{-1}\left(\frac{F(I_m) - F(I_n)^* F(h)}{(1 - F(h)^2)}\right) \quad \text{Equation 1}$$

$$I_2 = F^{-1}\left(\frac{F(I_n) - F(I_m)^* F(h)}{(1 - F(h)^2)}\right) \quad \text{Equation 2}$$

In the above equations, $I_1$ and $I_2$ are, respectively light actually emitted from reaction sites at different elevations (e.g., in a configuration shown in FIGS. 9A-9B, $I_1$ may be light emitted from reaction sites 964, while $I_2$ may be light emitted from reaction sites 962). $I_m$ is the light captured by the camera having a focal plane corresponding to the elevation of the reaction sites that emit $I_1$, while $I_n$ is the light captured by the camera having a focal plane corresponding to the elevation of the reaction sites that emit $I_2$. h is the kernel (also sometimes referred to as a point spread function, or PSF) reflecting the blurriness of the reaction sites which are out of focus, and can be determined through modeling based on the fact that the focal plane, the wavelength of emitted light, the magnification, the numerical aperture of the objective, and the height difference between reaction sites are known. h may also be experimentally, for example, using raytracing in an optical system and/or techniques such as described in U.S. Pat. App. No. 63/221,236, entitled "Methods and Systems for Real Time Extraction of Crosstalk in Illumination Emitted from Reaction Sites", filed on Jul. 13, 2021, the disclosure of which is incorporated by reference in its entirety. h may also be approximated using a Gaussian or first order Bessel function (Airy function). F is the Fourier transform, and $F^{-1}$ is the inverse Fourier transform.

To illustrate how equations 1 and 2 would operate to remove background illumination (i.e., illumination from out of focus reaction sites) consider the information that could be captured by an optics system such as those illustrated in FIGS. 9A-12B. For example, when an optics system simultaneously captures two images having different focal planes, those images can be represented as the light from the in-focus reaction sites, combined with the light from the out of focus reaction sites when that light is convolved with the blur kernel. This can be stated formally using the same symbols as equations 1 and 2 and with the $\circledast$ operator used to represent convolution using equations 3 and 4, below.

$$I_m = I_1 + I_2 \circledast h \quad \text{Equation 3}$$

$$I_n = I_2 + I_1 \circledast h \quad \text{Equation 4}$$

$I_2$ can then be solved for by subtracting $I_1 \circledast h$ from both sides of equation 4. This can then be plugged back into equation 3, providing equation 5, in which the only unknown is $I_1$. $I_n \circledast h$ can then be subtracted from both sides of equation 5, providing equation 6, in which the unknown value ($I_1$) is on the right side of the equation, while the captured images ($I_m$ and $I_n$) are on the right side of the equation.

$$I_m = I_1 + (I_n - I_1 \circledast h) \circledast h \quad \text{Equation 5}$$

$$I_m - I_n \circledast h = I_1 - (I_1 \circledast h) \circledast h \quad \text{Equation 6}$$

The convolution operator can then be removed from equation 6 by taking the Fourier transform of both sides and replacing convolution with multiplication since the Fourier transform of a convolution is the product of Fourier transforms. This is shown below in equations 7 and 8.

$$F(I_m - I_n \circledast h) = F(I_1 - (I_1 \circledast h) \circledast h) \quad \text{Equation 7}$$

$$F(I_m) - F(I_n)^* F(h) = F(I_1) - F(I_1)^* F(h)^* F(h) \quad \text{Equation 8}$$

The unknown value ($I_1$) can then be isolated by factoring $1 - F(h)^2$ from the right side of equation 8, to obtain equation 9, and then dividing both sides of equation 9 by $1 - F(h)^2$ and flipping the result to obtain equation 10.

$$F(I_m) - F(I_n)^* F(h) = F(I_1)^* (1 - F(h)^2) \quad \text{Equation 9}$$

$$F(I_1) = \frac{F(I_m) - F(I_n)^* F(h)}{(1 - F(h)^2)} \quad \text{Equation 10}$$

Finally, equation 1 can be obtained by taking the inverse Fourier transform of equation 10, there by providing a way to extract the light from a set of in-focus reaction sites from an image where those rection sites are in-focus (i.e., $I_m$) an image where those reaction sites are out of focus (i.e., $I_n$), and the blur kernel reflecting how out of focus the out of focus reaction sites are (i.e., h). Similar manipulations can be applied to obtain equation 2, in which light from the reaction sites which are in focus is $I_2$ rather than $I_1$.

Returning now to FIG. 16, after the background illumination has been removed in block 1902, in block the filtered images (i.e., the images with background images removed) may be combined in block 1903 to obtain a single super resolution image showing light emitted from all of the reaction sites. Finally, in block 1904, the super-resolution image can be provided as output of the process, such as for use in sequencing by synthesis or other types of processing. Alternatives are also possible. For example, in some implementations, the creation of a combined super-resolution image may be omitted, and instead any further processing may be performed directly on the filtered images obtained in block 1902. Accordingly, the description set forth above regarding the process of FIG. 16 should be understood as being illustrative only, and should not be treated as limiting.

Alternatives beyond omitting creation of a combined super-resolution image may also be possible. For example, in equations 1 and 2, the blur kernel was treated as being the same for each image. However, this is not a requirement for all potential implementations. For instance, in some implementations, rather than using equations 1 and 2, background illumination may be removed using equations 11 and 12, below.

$$I_1 = F^{-1}\left(\frac{F(I_m) - F(I_n)^* F(h_1)}{(1 - F(h_1)^* F(h_2))}\right) \quad \text{Equation 11}$$

$$I_2 = F^{-1}\left(\frac{F(I_n) - F(I_m)^* F(h_2)}{(1 - F(h_2)^* F(h_1))}\right) \quad \text{Equation 12}$$

In those equations, $h_1$ represents the blurriness of the background illumination in image $I_n$, while $h_2$ represents the blurriness of background illumination in image $I_m$.

Similarly, the approaches to removing background illumination in the case of a flow cell having two elevations which were discussed in the context of equations 1-12 can be extended to any number of elevations, since in each case the number of equations and unknowns would be the same (i.e., the same as the number of elevations) and so could be solved in a manner similar to that set forth above for the two elevation case. For instance, in the three elevation case, the captured images can be represented by equations 13-15 below:

$$I_L = I_1 + I_2 \circledast h_{L2} + I_3 \circledast h_{L3} \quad \text{Equation 13}$$

$$I_M = I_1 \circledast h_{M1} + I_2 + I_3 \circledast h_{M3} \quad \text{Equation 14}$$

$$I_N = I_1 \circledast h_{N1} + I_2 \circledast h_{N2} + I_3 \quad \text{Equation 15}$$

In equations 13-15, $I_1$ and $I_2$ have the same meanings as in Equations 1-12. $I_3$ is the illumination emitted from reaction sites at a third elevation which is different from the elevations of the reaction sites which emit $I_1$ and $I_2$. $I_L$ is the image captured with the reaction sites that emit $I_1$ in focus, $I_M$ is the image captured with the reaction sites that emit $I_2$ in focus, and $I_N$ is the image captured with the reaction sites that emit $I_3$ in focus. $h_{L2}$ and $h_{L3}$ are, respectively, kernels representing the blurriness of $I_2$ and $I_3$ in the image $I_L$. By applying calculations similar to those described above in the context of equations 3-12, equations 13-15 can be used to derive equations expressing any of the unknown in terms of other known values. The result of this type of derivation for I3 is shown below in equation 16.

$$\text{Equation 16}$$

$$I_3 = F^{-1}\left(\frac{\begin{array}{l}(F(h_{L2})^* F(h_{M1})^* F(h_{N1}) - F(h_{M1})^* F(h_{N2}))^* F(I_M) - \\ (F(h_{N1})^* F(h_{M1}) - F(h_{M1})^{2*} F(h_{N2}))^* F(I_L) + \\ (F(h_{M1}) - F(h_{L2})^* F(h_{M1})^2)^* F(I_N)\end{array}}{\begin{array}{l}(F(h_{M3}) - F(h_{L3})^* F(h_{M1}))^* \\ (F(h_{N1}) - F(h_{M1})^* F(h_{N2})) - \\ (F(h_{M3})^* F(h_{N1}) - F(h_{M1}))^*(1 - F(h_{L2})^* F(h_{M1}))\end{array}}\right)$$

V. Miscellaneous

It is to be understood that the subject matter described herein is not limited in its application to the details of construction and the arrangement of components set forth in the description herein or illustrated in the drawings hereof. The subject matter described herein is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

When used in the claims, the term "set" should be understood as one or more things which are grouped together. Similarly, when used in the claims "based on" should be understood as indicating that one thing is determined at least in part by what it is specified as being "based on". Where one thing is required to be exclusively determined by another thing, then that thing will be referred to as being "exclusively based on" that which it is determined by.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "above," "below," "front," "rear," "distal," "proximal," and the like) are only used to simplify description of one or more examples described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described examples (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and instead illustrations. Many further examples will be apparent to those of skill in the art upon reviewing the above description. The scope of the disclosed subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) paragraph, unless and until such claim limitations expressly use the phrase "means for" followed by a statement of function void of further structure.

In the claims, the phrase "means for obtaining a plurality of differently focused unfiltered images based on signals from reaction sites comprised by a flow cell" should be understood as a means plus function limitation in which the function is "obtaining a plurality of differently focused unfiltered images based on signals from reaction sites comprised by a flow cell" and the corresponding structure is one or more cameras, beam splitters and other components illustrated and/or discussed in the context of FIGS. 9A-12B.

In the claims, the phrase "means for determining a plurality of derived images separating signals from corresponding sets of reaction sites based on differences in focus" should be understood as a means plus function limitation in which the function is "determining a plurality of derived images separating signals from corresponding sets of reaction sites based on differences in focus" and the corresponding structure is a computer configured to filter unfocused background illumination as described in the context of equations 1-2, 11-16, and the surrounding description.

The following claims recite aspects of certain examples of the disclosed subject matter and are considered to be part of the above disclosure. These aspects may be combined with one another.

What is claimed is:

1. A system comprising:
a flow cell comprising a plurality of reaction sites a fluid inlet port and a fluid outlet port, wherein:
the plurality of reaction sites comprises a plurality of sets of reaction sites;
for each set of reaction sites from the plurality of sets of reaction sites:
that set of reaction sites is a subset of the plurality of reaction sites;
that set of reaction sites has a corresponding elevation relative to a bottom of the flow cell;
each reaction site comprised by that set of reaction sites is disposed on either a bottom surface of a corresponding well or a surface above the bottom surface of the corresponding well, and is located at that set of reaction sites' corresponding elevation relative to the bottom of the flow cell; and
no reaction site from any set of reaction sites other than that set of reaction sites is located at that set of reaction sites' corresponding elevation relative to the bottom of the flow cell;
a set of cameras; and
a processor connected to the set of cameras and programmed to:
receive a plurality of unfiltered images captured by the set of cameras, wherein the plurality of unfiltered images comprises, for each set of reaction sites from the plurality of sets of reaction sites, an image corresponding to that set of reaction sites; and
for each set of reaction sites from the plurality of sets of reaction sites, determine a derived image corresponding to that set of reaction sites, wherein the derived image corresponding to that set of reaction sites is based on using differences in focus between images from the plurality of unfiltered images to remove signals from reaction sites not comprised by that set of reaction sites while retaining signals from reaction sites comprised by that set of reaction sites;
wherein:
each set of reaction sites from the plurality of sets of reaction sites is disjoint with all other sets of reaction sites from the plurality of sets of reaction sites; and
for each image from the plurality of unfiltered images, that image depicts:
light emitted from reaction sites comprised by the set of reaction sites corresponding to that image; and
light emitted from reaction sites not comprised by the set of reaction sites corresponding to that image.

2. The system of claim 1, wherein:
for each reaction site from the plurality of reaction sites, that reaction site has a center;
for each reaction site in the plurality of reaction sites, there is an adjacent reaction site in the plurality of reaction sites, wherein a distance between the center of that reaction site and the center of the adjacent reaction site is less than a diffraction limit for a wavelength of light used in obtaining the plurality of unfiltered images; and
for each set of reaction sites from the plurality of sets of reaction sites, for each reaction site in that set of reaction sites, there is a neighboring reaction site in that set of reaction sites, wherein a distance between the center of that reaction site and the center of the neighboring reaction site is greater than the diffraction limit for the wavelength of light used in obtaining the plurality of unfiltered images.

3. The system of claim 1, wherein, for each set of reaction sites from the plurality of sets of reaction sites, the set of cameras comprises a corresponding camera focused with a focal plane at that set of reaction sites' corresponding elevation relative to the bottom of the flow cell.

4. The system of claim 3, wherein the system comprises a one or more beam splitters to direct signals from the plurality of reaction sites to the cameras from the set of cameras.

5. The system of claim 1, wherein the processor is programmed to:
cause a first camera from the set of cameras to capture a first unfiltered image, wherein the first unfiltered image corresponds to a first set of reaction sites from the plurality of sets of reaction sites, and wherein the first camera is focused on a first focal plane at the first set of reaction sites' corresponding elevation relative to the bottom of the flow cell when it is caused to capture the first unfiltered image;
refocus the first camera on a second focal plane at the second set of reaction sites' corresponding elevation from the bottom of the flow cell; and
cause the first camera to capture a second unfiltered image, wherein the second unfiltered image corresponds to the second set of reaction sites, and wherein the first camera is focused on a second focal plane at the second set of reaction sites' corresponding elevation from the bottom of the flow cell when it is caused to capture the second unfiltered image.

6. The system of claim 1, wherein:
the set of cameras comprises a line scan camera;
the line scan camera comprises a plurality of sets of sensors, wherein, for each set of sensors from the plurality of sets of sensors:
that set of sensors has a corresponding set of reaction sites from the plurality of sets of reaction sites; and
that set of sensors is focused on a focal plane at its corresponding set of reaction sites' corresponding elevation relative to the bottom of the flow cell; and
the processor is programmed to cause the line scan camera to:
capture a first unfiltered image using a first set of sensors, wherein the first set of sensors corresponds to a first set of reaction sites from the plurality of sets of reaction sites; and
capture a second unfiltered image using a second set of sensors, wherein the second set of sensors corresponds to a second set of reaction sites from the plurality of sets of reaction sites.

7. The system of claim 1, wherein:
  each set of reaction sites from the plurality of sets of reaction sites has a corresponding point spread function; and
  for each set of reaction sites from the plurality of sets of reaction sites, determining the derived image corresponding to that set of reaction sites comprises, for each other set of reaction sites from the plurality of sets of reaction sites, removing signals from reaction sites comprised by that other set of reaction sites using the unfiltered image corresponding to that other set of reaction sites and the point spread function corresponding to that other set of reaction sites.

8. The system of claim 7, wherein, for at least one set of reaction sites from the plurality of sets of reaction sites, the corresponding point spread function for that set of reaction sites is different from the corresponding point spread functions for all other sets of reaction sites from the plurality of sets of reaction sites.

9. The system of claim 7, wherein, for at least one set of reaction sites from the plurality of sets of reaction sites, the corresponding point spread function for that set of reaction sites is the same as the corresponding point spread function for at least one other set of reaction sites from the plurality of sets of reaction sites.

10. The system of claim 1, wherein the plurality of sets of reaction sites consists of two sets of reaction sites.

11. The system of claim 1, wherein the plurality of sets of reaction sites comprises three or more sets of reaction sites.

12. The system of claim 1, wherein, for each set of reaction sites from the plurality of sets of reaction sites, for each reaction site comprised by that set of reaction sites, that reaction site is located in a corresponding well comprised by the flow cell.

13. The system of claim 1, wherein, for each set of reaction sites from the plurality of sets of reaction sites, for each reaction site comprised by that set of reaction sites, that reaction site is located on a corresponding post comprised by the flow cell.

* * * * *